（12） United States Patent
Sasaki

(10) Patent No.: US 10,406,258 B2
(45) Date of Patent: Sep. 10, 2019

(54) HOLLOW FIBER MEMBRANE BUNDLE, ARTIFICIAL LUNG, AND METHOD OF MANUFACTURING HOLLOW FIBER MEMBRANE

(71) Applicant: TERUMO KABUSHIKI KAISHA, Tokyo (JP)

(72) Inventor: Eisuke Sasaki, Elkton, MD (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 100 days.

(21) Appl. No.: 15/413,765

(22) Filed: Jan. 24, 2017

(65) Prior Publication Data

US 2017/0128621 A1    May 11, 2017

Related U.S. Application Data

(63) Continuation of application No. PCT/JP2015/068200, filed on Jun. 24, 2015.

(30) Foreign Application Priority Data

Aug. 6, 2014   (JP) .................................. 2014-160828

(51) Int. Cl.
  *A61M 1/16*      (2006.01)
  *A61L 27/16*     (2006.01)
  (Continued)

(52) U.S. Cl.
  CPC ............... *A61L 27/16* (2013.01); *A61L 27/50* (2013.01); *A61M 1/1698* (2013.01);
  (Continued)

(58) Field of Classification Search
  CPC ...... A61L 27/16; A61L 27/50; A61L 2400/12; D01D 63/021; D01D 63/025; D01D 63/063; A61M 1/1698; A61M 2205/75
  See application file for complete search history.

(56) References Cited

U.S. PATENT DOCUMENTS 4,881,955 A   11/1989   Bikson et al.
4,911,846 A   3/1990    Akasu et al.
              (Continued)

FOREIGN PATENT DOCUMENTS

EP   1108462 A2   6/2001
EP   2692370 A1   2/2014
              (Continued)

OTHER PUBLICATIONS

European Office Action, PCT/JP2015068200, dated Apr. 10, 2018.

*Primary Examiner* — Benjamin J Klein
(74) *Attorney, Agent, or Firm* — MacMillan, Sobanski & Todd, LLC

(57) ABSTRACT

A hollow fiber membrane bundle configured to be used in an artificial lung and comprised of integrated hollow fiber membranes 31 has hollow portions through which a fluid passes. The hollow fiber membrane bundle is shaped as a cylinder body. In addition, the hollow fiber membrane 31 is tilted with respect to a central axis O of the cylinder body, is wound around the central axis O of the cylinder body, and satisfies the following conditions. An inner diameter $\phi d_1$ of the hollow fiber membrane 31 is equal to or smaller than 150 μm, a tilt angle θ with respect to the central axis O of the cylinder body of the hollow fiber membrane 31 is equal to or smaller than 60°, and a ratio $\phi D_1/L$ of an outer diameter $\phi D_1$ of the cylinder body to a length L of the cylinder body is equal to or greater than 0.4.

2 Claims, 14 Drawing Sheets

(51) Int. Cl.
*A61L 27/50* (2006.01)
*D01F 6/06* (2006.01)
*B01D 63/02* (2006.01)
*B01D 63/04* (2006.01)

(52) U.S. Cl.
CPC ......... *B01D 63/021* (2013.01); *B01D 63/025* (2013.01); *B01D 63/043* (2013.01); *D01F 6/06* (2013.01); *A61L 2400/12* (2013.01); *A61M 2205/75* (2013.01); *B01D 2313/22* (2013.01); *B01D 2319/06* (2013.01); *D10B 2321/022* (2013.01); *D10B 2509/00* (2013.01)

(56) References Cited

U.S. PATENT DOCUMENTS

| | | | | |
|---|---|---|---|---|
| 6,004,511 A | * | 12/1999 | Biscegli | A61M 1/1698 422/44 |
| 2007/0231203 A1 | * | 10/2007 | Mizoguchi | A61M 1/1698 422/45 |
| 2012/0277654 A1 | * | 11/2012 | Olson | A61M 1/1698 604/6.09 |
| 2014/0030146 A1 | | 1/2014 | Takeuchi | |
| 2015/0010433 A1 | | 1/2015 | Takeuchi et al. | |

FOREIGN PATENT DOCUMENTS

| | | |
|---|---|---|
| JP | 2001178818 | 3/2001 |
| WO | 9303828 | 3/1993 |

* cited by examiner

HOLLOW FIBER MEMBRANE BUNDLE, ARTIFICIAL LUNG, AND METHOD OF MANUFACTURING HOLLOW FIBER MEMBRANE

CROSS REFERENCE TO RELATED APPLICATIONS

This application is a continuation of PCT Application No. PCT/JP2015/068200, filed Jun. 24, 2015, based on and claiming priority to Japanese application no. 2014-160828, filed Aug. 6, 2014, both of which are incorporated herein by reference in their entirety.

TECHNICAL FIELD

The present invention relates to a hollow fiber membrane bundle, an artificial lung, and a method of manufacturing a hollow fiber membrane bundle.

BACKGROUND OF THE INVENTION

In the related art, there is a known artificial lung having a hollow fiber membrane bundle which is configured with multiple hollow fiber membranes (for example, U.S. Pat. No. 4,911,846). U.S. Pat. No. 4,911,846 discloses a hollow fiber membrane bundle having a bamboo blind shape in which multiple hollow fiber membranes are disposed substantially in parallel so as to serve as the weft and the weft is interwoven with the warp. A hollow fiber sheet having such a bamboo blind shape is folded such that the hollow fiber membrane bundle can have a prismatic shape or a columnar shape as the outer shape.

In the hollow fiber membrane bundle having such a configuration, there is concern that gas exchange or heat exchange may be insufficient in a portion where the weft (hollow fiber membranes) and the warp (warp threads) overlap each other. In addition, there is concern that blood is likely to stay and a thrombus may be formed in the portion where the weft and the warp overlap each other.

In order to solve the foregoing problems, it is preferable that the hollow fiber membranes are wound manyfold on the outer periphery of a round rod body, for example, around a central axis thereof so as to be a hollow fiber membrane bundle having a cylindrical body shape.

However, as the number of times of winding the hollow fiber membranes increases, the total volume of gaps between the hollow fiber membranes increases. As a result thereof, the amount of blood passing through the gaps, that is, the blood filling amount also increases. Accordingly, a burden to a patient (i.e., the priming volume of the membrane bundle) becomes significant.

Therefore, it is possible to consider using a hollow fiber membrane having a small outer diameter. Accordingly, while the surface area of the hollow fiber membrane which comes into contact with blood is maintained, the total volume of the gaps between the hollow fiber membranes can be prevented from increasing and the blood filling amount can be reduced.

However, when the outer diameter of the hollow fiber membrane is reduced, the inner diameter is also reduced. Therefore, a pressure loss of a fluid pas sing through the inside of the hollow fiber membrane increases. If the pressure loss of a fluid increases, for example, in a case of an artificial lung section, there is concern that gas may flow out from the hollow fiber membrane to the outside.

SUMMARY OF THE INVENTION

An object of the present invention is to provide a hollow fiber membrane bundle and a method of manufacturing a hollow fiber membrane bundle, in which an excessive pressure loss of a fluid inside a hollow fiber membrane is avoided, and a blood filling amount can also be reduced, and thus, a burden to a patient can be reduced.

The object is realized as described below according to first aspect of the present invention.

A hollow fiber membrane bundle configured to be used in an artificial lung is comprised of integrated hollow fiber membranes having hollow portions through which a fluid passes, the hollow fiber membrane bundle exhibiting a shape of a cylindrical body as a whole shape.

The hollow fiber membrane is tilted with respect to a central axis of the cylinder body and is wound around the central axis of the cylinder body, wherein an inner diameter $\phi d_1$ of the hollow fiber membrane is preferably equal to or smaller than 150 μm. A tilt angle θ with respect to the central axis of the cylinder body of the hollow fiber membrane is preferably equal to or smaller than 60°. A ratio $\phi D_1/L$ of an outer diameter $\phi D_1$ of the cylinder body to a length L of the cylinder body is preferably equal to or greater than 0.4.

In the hollow fiber membrane bundle, the inner diameter $\phi d_1$ may preferably range from 90 μm to 150 μm.

In the hollow fiber membrane bundle, the tilt angle θ may preferably range from 30° to 60°.

In the hollow fiber membrane bundle, the ratio $\phi D_1/L$ may preferably range from 0.4 to 2.5.

In the hollow fiber membrane bundle, the outer diameter $\phi D_1$ may preferably range from 20 mm to 200 mm. The length L preferably ranges from 30 mm to 250 mm.

In the hollow fiber membrane bundle, an outer diameter $\phi d_2$ of the hollow fiber membrane may preferably range from 120 μm to 220 μm.

In the hollow fiber membrane bundle, an inner diameter $\phi D_2$ of the cylinder body may preferably range from 10 mm to 150 mm.

An artificial lung of the invention includes the hollow fiber membrane bundle as described above.

The present invention further provides a method of manufacturing a hollow fiber membrane bundle configured to be used in an artificial lung and comprised of integrated hollow fiber membranes having hollow portions through which a fluid passes, wherein the hollow fiber membrane bundle exhibits a shape of a cylindrical body as a whole shape. The method comprises winding a hollow fiber membrane having an inner diameter $\phi d_1$ equal to or smaller than 150 μm around a central axis of the cylinder body such that a tilt angle θ with respect to the central axis of the cylinder body becomes equal to or smaller than 60° and a ratio $\phi D_1/L$ of an outer diameter $\phi D_1$ of the cylinder body to a length L of the cylinder body becomes equal to or greater than 0.4.

Effect of Invention

According to a first aspect of the present invention, even if a hollow fiber membrane having a relatively small inner diameter (equal to or smaller than 150 μm) is used, since the tilt angle θ with respect to the central axis of the cylinder body of the hollow fiber membrane is set to equal to or smaller than 60° and the ratio $\phi D_1/L$ of the outer diameter $\phi D_1$ of the cylinder body to the length L of the cylinder body is set to equal to or greater than 0.4, the overall length of the hollow fiber membrane can be prevented from being excessively elongated. Therefore, in the hollow fiber membrane bundle, a pressure loss of the fluid can be reduced and a blood filling amount is reduced. Thus, a burden to a patient can be reduced.

DETAILED DESCRIPTION OF PREFERRED EMBODIMENTS

Hereinafter, a hollow fiber membrane bundle, an artificial lung, and a method of manufacturing a hollow fiber membrane bundle, according to the present invention will be described in detail based on favorable embodiments illustrated in the accompanying drawings.

First Embodiment

Note that, the left sides in FIGS. 1, 3, 4 and 8 will be referred to as "left" or "leftward (one side)" and the right sides therein will be referred to as "right" or "rightward (the other side)". In addition, in FIGS. 1 to 6, the inside of the artificial lung will be described as "blood inflow side" or "upstream side" and the outside thereof will be described as "blood outflow side" or "downstream side". In addition, for convenience of description, in FIG. 9 (and similarly in FIGS. 13 and 14 as well), an X-axis, a Y-axis, and a Z-axis are illustrated as three axes orthogonal to each other.

First, a description will be given regarding the artificial lung to which the hollow fiber membrane bundle of the present invention is applied.

An artificial lung 10 illustrated in FIGS. 1 to 5 has a substantially columnar shape as the whole shape. The artificial lung 10 is an artificial lung that is equipped with a heat exchanger and includes a heat exchange section 10B which is internally provided and performs heat exchange with respect to blood; and an artificial lung section 10A which serves as a gas exchange section, is provided on the outer peripheral side of the heat exchange section 10B, and performs gas exchange with respect to the blood. For example, the artificial lung 10 is used by being installed in an extracorporeal blood circulation loop.

The artificial lung 10 has a housing 2A, and the artificial lung section 10A and the heat exchange section 10B are accommodated inside the housing 2A.

The housing 2A is configured to have a cylindrical housing main body 21A, a disk-shaped first lid 22A which seals a left end opening of the cylindrical housing main body 21A, and a disk-shaped second lid 23A which seals a right end opening of the cylindrical housing main body 21A.

The cylindrical housing main body 21A, the first lid 22A, and the second lid 23A are formed of resin materials. The first lid 22A and the second lid 23A are fixedly attached to the cylindrical housing main body 21A through a method such as welding or bonding which is performed by using an adhesive.

A pipe-shaped blood outflow port 28 is formed in an outer peripheral portion of the cylindrical housing main body 21A. The blood outflow port 28 protrudes substantially in a tangential direction of an outer peripheral surface of the cylindrical housing main body 21A (refer to FIG. 5).

Figure 1:
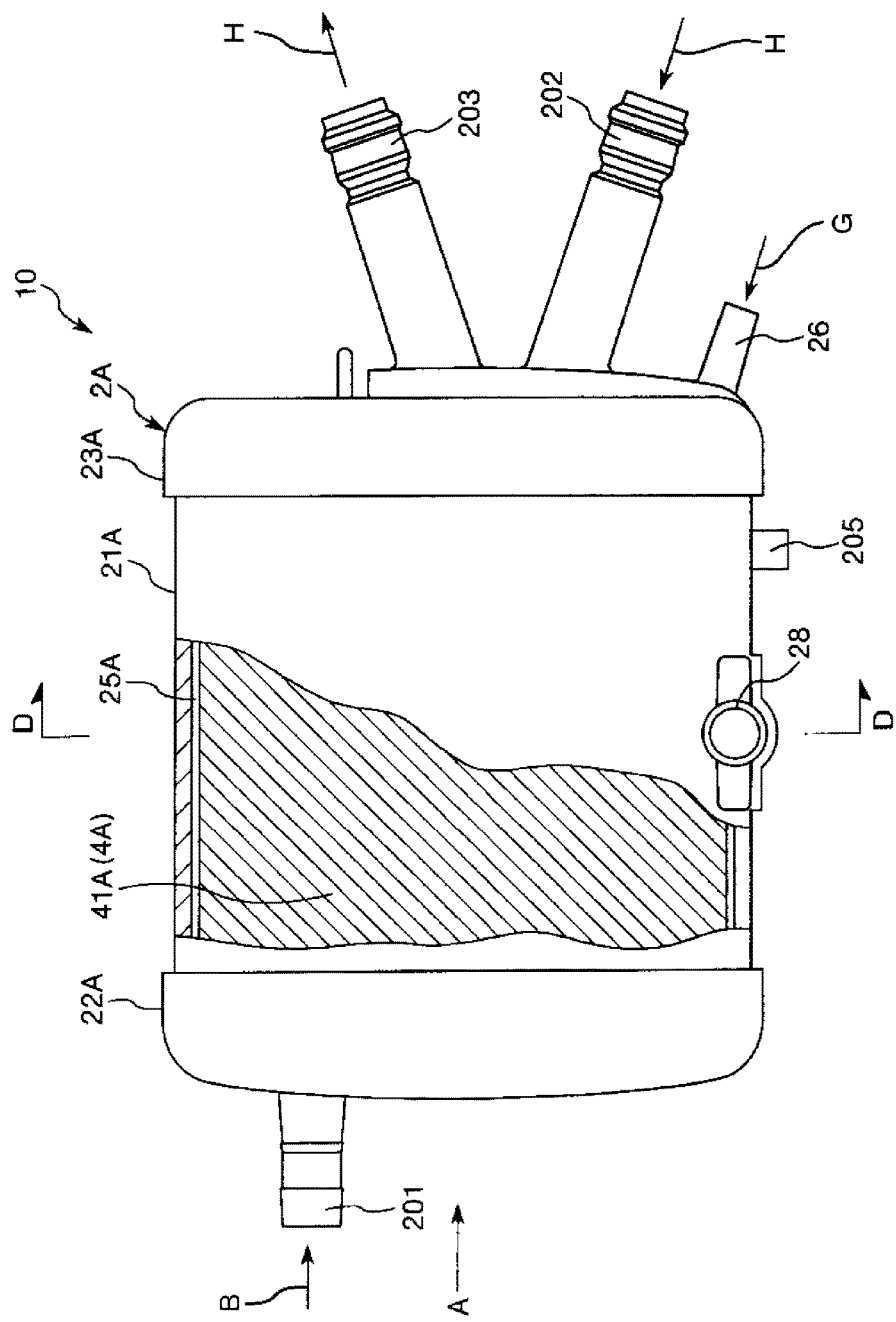
FIG. 1 is a plan view of an artificial lung to which a hollow fiber membrane bundle of the present invention is applied.
Figure 2:
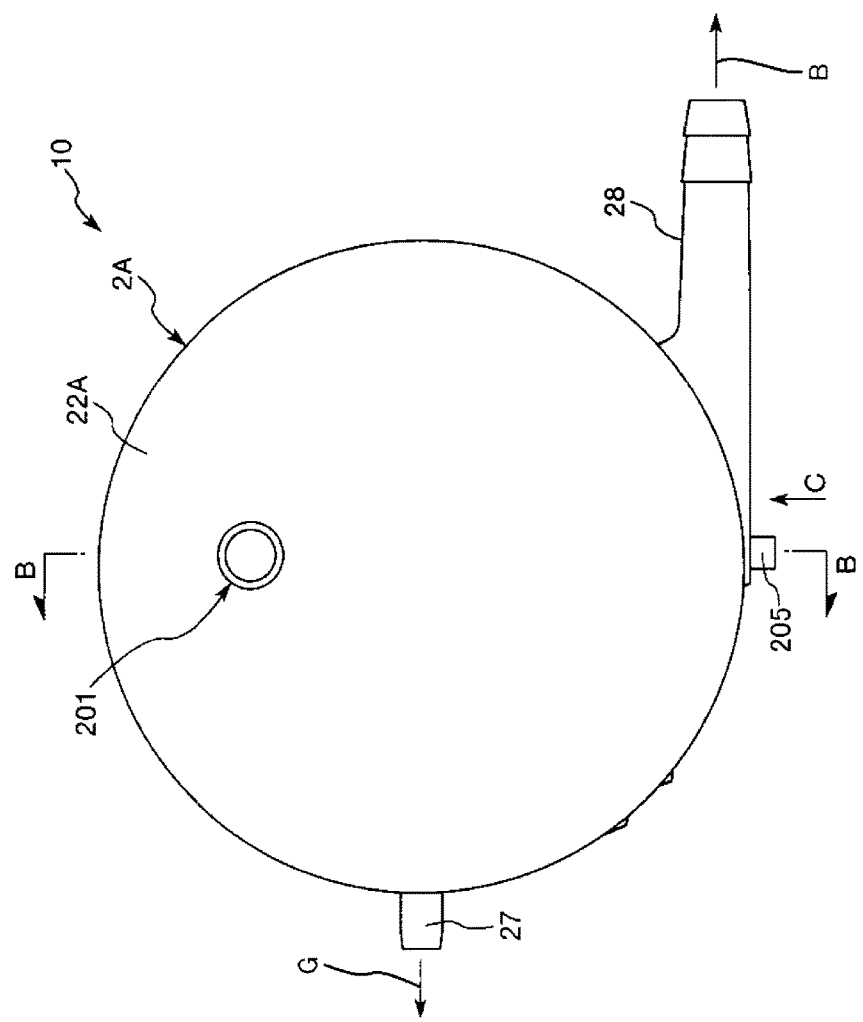
FIG. 2 is a view when the artificial lung illustrated in FIG. 1 is viewed in an arrow A direction.
Figure 3:
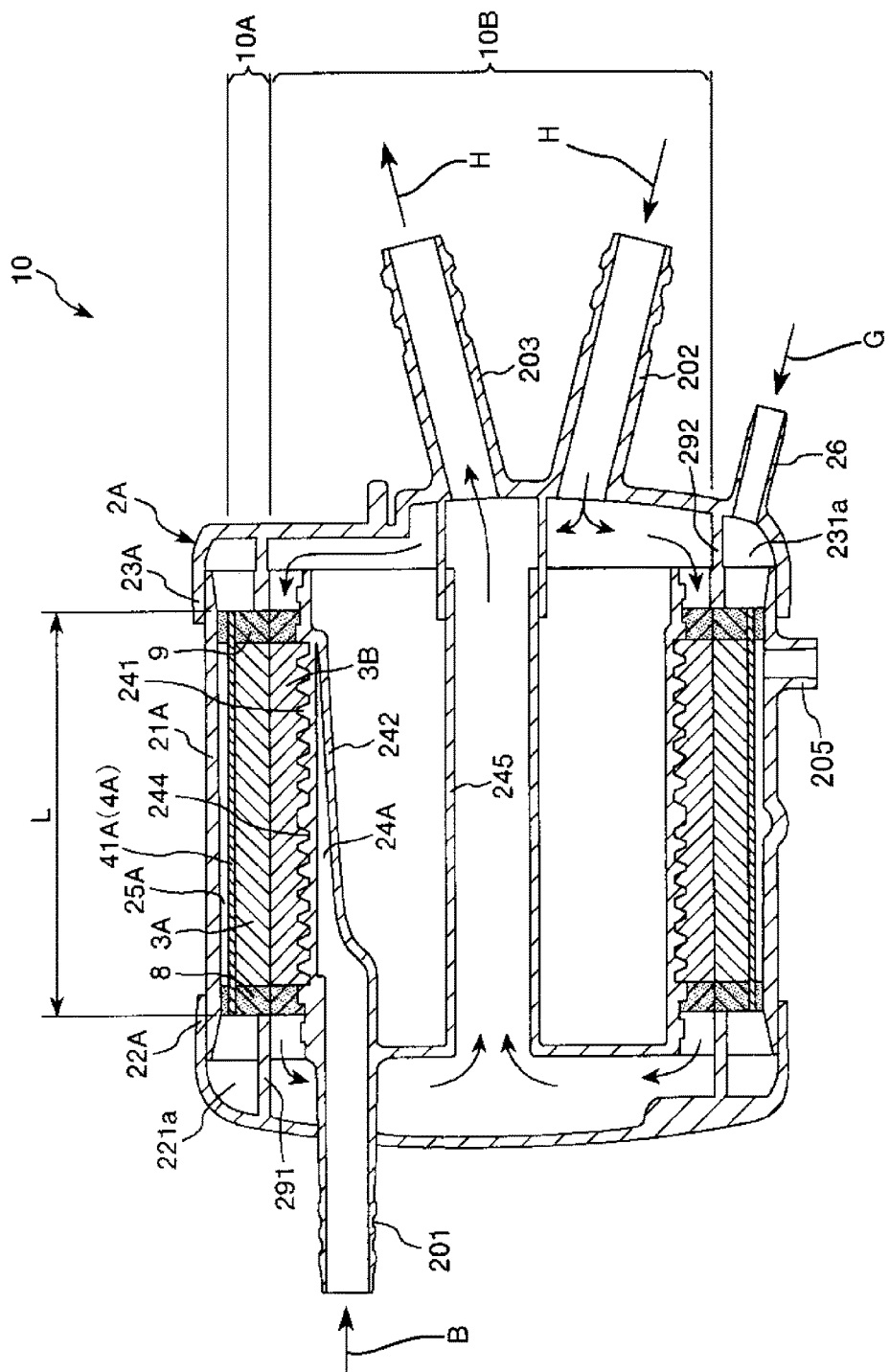
FIG. 3 is a cross-sectional view taken along line B-B in FIG. 2.
Figure 4:
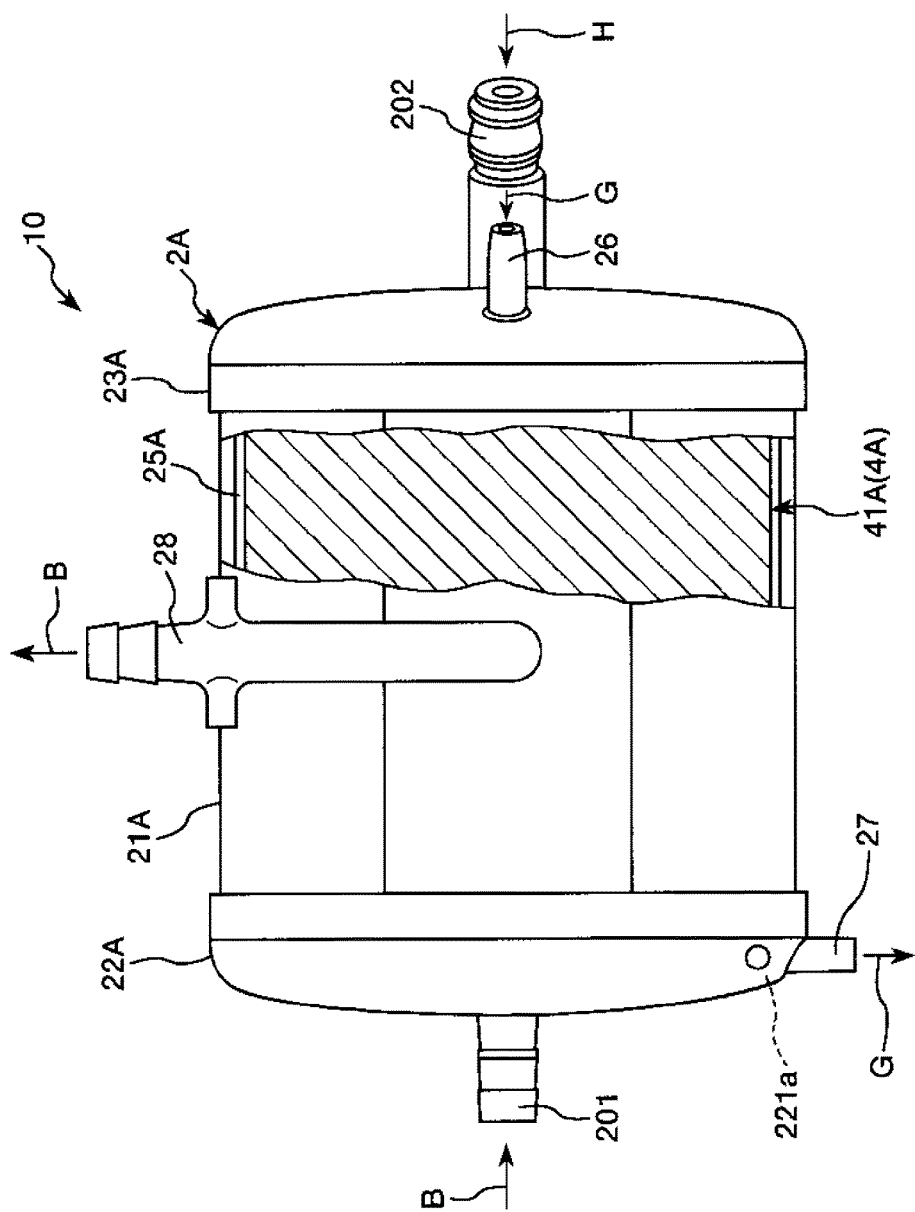
FIG. 4 is a view when viewed in an arrow C direction in FIG. 2.

In addition, as illustrated in FIGS. 1 to 3, a pipe-shaped purge port 205 is protrusively formed in the outer peripheral portion of the cylindrical housing main body 21A. The purge port 205 is formed in the outer peripheral portion of the cylindrical housing main body 21A such that a central axis thereof intersects a central axis of the cylindrical housing main body 21A.

A pipe-shaped gas outflow port 27 is protrusively formed in the first lid 22A. In addition, a blood inflow port 201 protrudes from an end surface of the first lid 22A such that a central axis thereof becomes eccentric with respect to the center of the first lid 22A.

The gas outflow port 27 is formed in the outer peripheral portion of the first lid 22A such that a central axis intersects the center of the first lid 22A (refer to FIG. 2).

A pipe-shaped gas inflow port 26, a heat medium inflow port 202, and a heat medium outflow port 203 are protrusively formed in the second lid 23A. The gas inflow port 26 is formed at an edge portion on the end surface of the second lid 23A. Each of the heat medium inflow port 202 and the heat medium outflow port 203 is formed substantially in a central portion on the end surface of the second lid 23A. In addition, the center lines of the heat medium inflow port 202 and the heat medium outflow port 203 are slightly tilted with respect to the center line of the second lid 23A.

Note that, in the present invention, the whole shape of the housing 2A is not necessarily a completely columnar shape.

For example, the housing 2A may have a shape partially lacking, a shape to which a variant portion is added, or the like.

Figure 5:
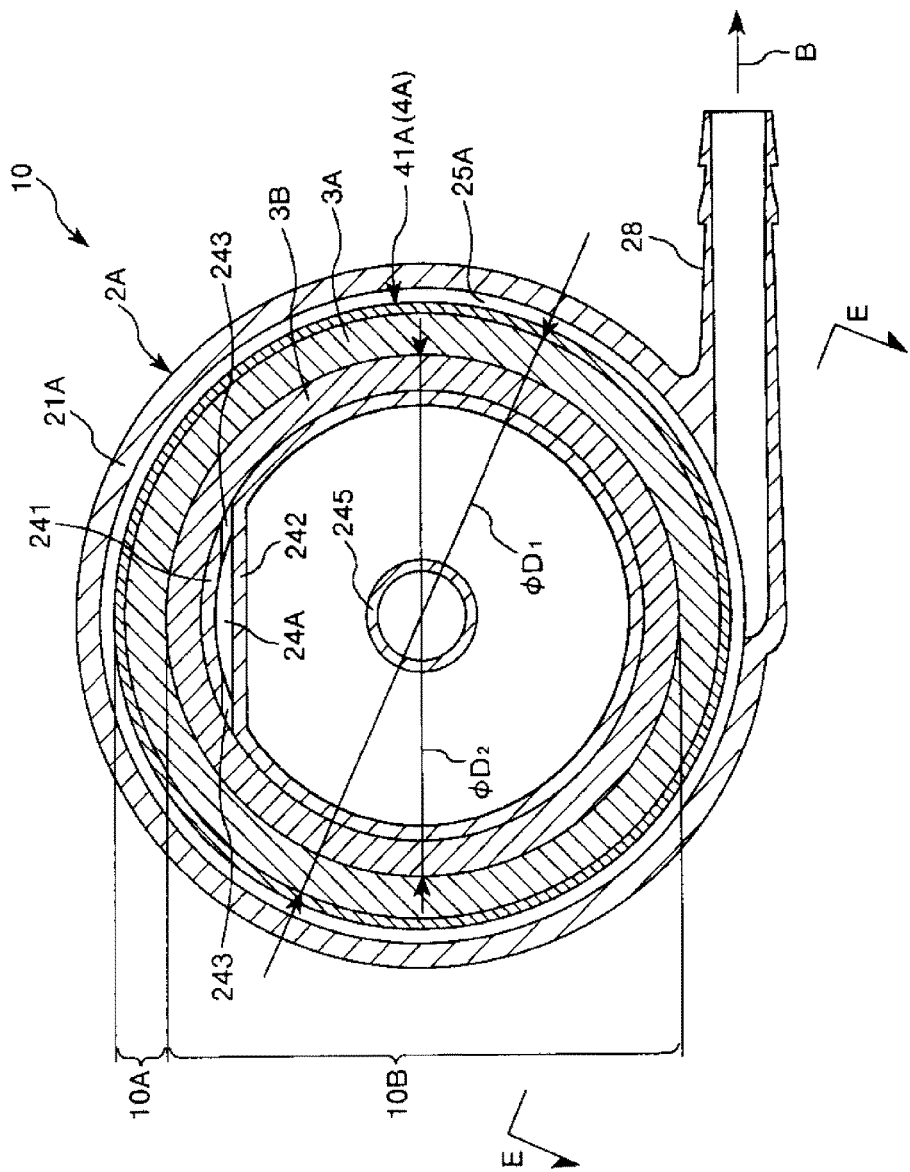
FIG. 5 is a cross-sectional view taken along line D-D in FIG. 1.

As illustrated in FIGS. 3 and 5, the cylindrical artificial lung section 10A is accommodated inside the housing 2A along the inner peripheral surface. The artificial lung section 10A is configured to have a cylindrical hollow fiber membrane bundle 3A and a filter member 41A which serves as air bubble removal means 4A provided on the outer peripheral side of the hollow fiber membrane bundle 3A. The hollow fiber membrane bundle 3A and the filter member 41A are disposed in the order of the hollow fiber membrane bundle 3A and the filter member 41A from the blood inflow side.

In addition, the cylindrical heat exchange section 10B is installed inside the artificial lung section 10A along the inner peripheral surface thereof. The heat exchange section 10B has a hollow fiber membrane bundle 3B.

Figure 6:
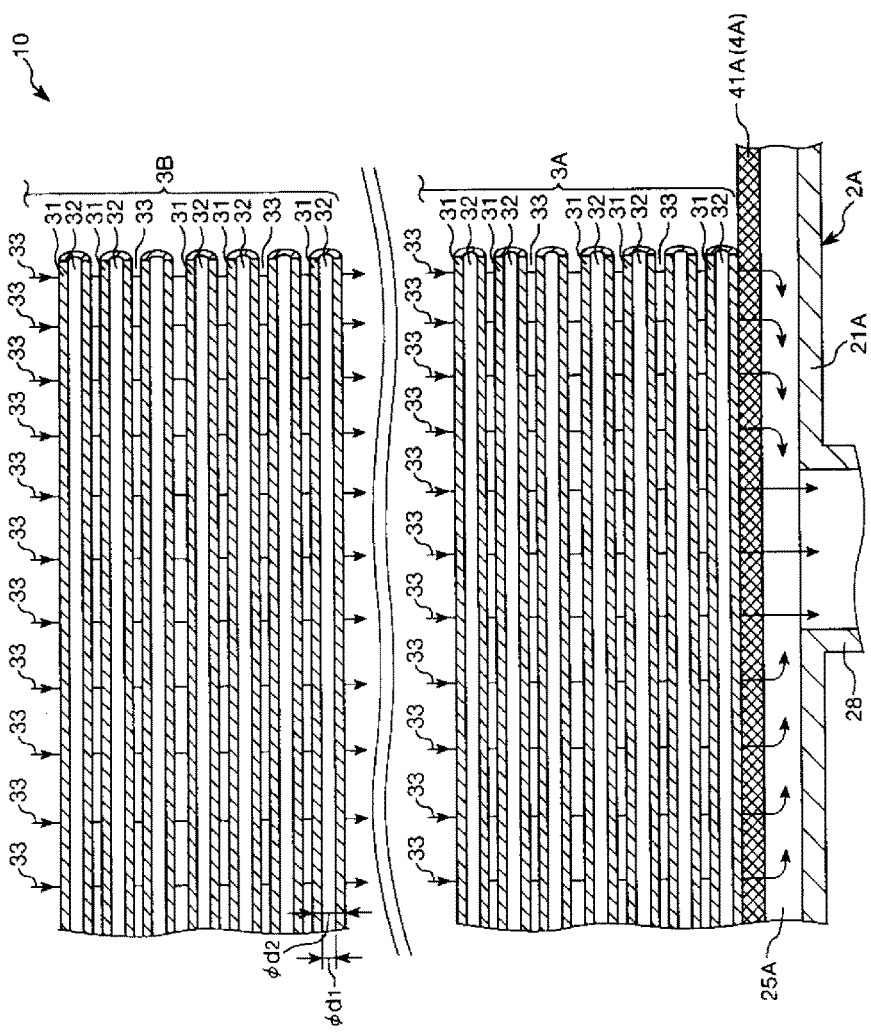
FIG. 6 is a cross-sectional view taken along line E-E in FIG. 5.

As illustrated in FIG. 6, each of the hollow fiber membrane bundles 3A and 3B is configured with multiple hollow fiber membranes 31 and is formed by integrating and laminating the hollow fiber membranes 31 in a layered manner. The number of laminated layers is not particularly limited. For example, it is preferable to have 3 to 40 layers. Note that, each of the hollow fiber membranes 31 of the hollow fiber membrane bundle 3A has a function of exchanging gas. Meanwhile, each of the hollow fiber membranes 31 of the hollow fiber membrane bundle 3B has a function of exchanging heat.

In the present invention, a relatively thin hollow fiber membrane is used as the hollow fiber membrane 31 of the hollow fiber membrane bundle 3A, and an inner diameter $\phi d_1$ of the hollow fiber membrane 31 is equal to or smaller than 150 μm. In addition, the inner diameter (maximum inner diameter) $\phi d_1$ preferably ranges from 90 μm to 150 μm and more preferably ranges from 100 μm to 130 μm. In a case where the inner diameter $\phi d_1$ is greater than 150 μm, it would be difficult to sufficiently reduce an outer diameter $\phi d_2$ of the hollow fiber membrane 31. In addition, in a case where the inner diameter $\phi d_1$ is smaller than the above-referenced lower limit value, there is concern that an increase of a pressure loss when gas G flows in flow paths 32 which are hollow portions of the hollow fiber membranes 31 may be caused.

In addition, the outer diameter (maximum outer diameter) $\phi d_2$ of the hollow fiber membrane 31 preferably ranges from 120 μm to 220 μm and more preferably ranges from 150 μm to 200 μm. In a case where the outer diameter $\phi d_2$ exceeds the above-referenced upper limit value, a gap between the hollow fiber membranes 31 adjacent to each other becomes significant, and thus, a filling amount of blood B flowing down the gap increases. Meanwhile, in a case where the outer diameter $\phi d_2$ is below the above-referenced lower limit value, it is difficult to sufficiently increase the inner diameter $\phi d_1$.

Note that, a ratio $\phi d_1/\phi d_2$ of the inner diameter $\phi d_1$ to the outer diameter $\phi d_2$ preferably ranges from 0.50 to 0.85 and more preferably ranges from 0.60 to 0.75.

The hollow fiber membrane 31 of the hollow fiber membrane bundle 3A is configured with a porous gas exchange membrane. The pore diameter of the hollow fiber membrane 31 preferably ranges from 0.01 μm to 5 μm and more preferably ranges from 0.01 μm to 1 μm. In addition, as the hollow fiber membrane 31, a hydrophobic polymer material such as polypropylene, polyethylene, polysulfone, polyacrylonitrile, polytetrafluoroethylene, and cellulose acetate is used. It is preferable to use a polyolefin-based resin, and it is particularly preferable to use polypropylene. In addition, the micropore of the hollow fiber membrane 31 can be formed through an extension method or a solid and liquid phase separation method, for example.

Note that, as the hollow fiber membrane 31 of the hollow fiber membrane bundle 3B, it is possible to use a hollow fiber membrane having an inner diameter ranging from 50 μm to 700 μm and an outer diameter ranging from 100 μm to 1,000 μm, approximately.

As illustrated in FIG. 3, both end portions of each of the hollow fiber membrane bundles 3A and 3B are collectively fixed to an inner surface of the cylindrical housing main body 21A through partition walls 8 and 9. For example, the partition walls 8 and 9 are configured with a potting material such as polyurethane and silicone rubber, an adhesive, or the like. Moreover, an inner peripheral portion of the hollow fiber membrane bundle 3B engages with an uneven portion 244 formed in the outer peripheral portion of a first cylinder member 241. Due to the engagement and the state of being fixed through the partition walls 8 and 9, the hollow fiber membrane bundle 3B is reliably fixed to the cylindrical housing main body 21A. Thus, it is possible to reliably prevent positional deviation of the hollow fiber membrane bundle 3B from occurring while the artificial lung 10 is in use. In addition, the uneven portion 244 also functions as a flow path for allowing the blood B to circumambulate the hollow fiber membrane bundle 3B in its entirety.

A blood flow path 33 through which the blood B flows from the upper side toward the lower side in FIG. 6 is formed outside each of the hollow fiber membranes 31 between the partition wall 8 and the partition wall 9 inside the housing 2A, that is, in the gap between the hollow fiber membranes 31.

A blood inflow side space 24A which serves as a blood inflow portion of the blood B flowed in through the blood inflow port 201 and communicates with the blood inflow port 201 is formed on the upstream side of the blood flow path 33 (refer to FIGS. 3 and 5).

The blood inflow side space 24A is a space defined by the cylindrical first cylinder member 241 and a plate piece 242 which is disposed inside the first cylinder member 241 and is disposed so as to face apart of the inner peripheral portion thereof. The blood B which has flowed into the blood inflow side space 24A can flow down through the blood flow path 33 in its entirety via multiple side holes 243 formed in the first cylinder member 241.

In addition, a second cylinder member 245 concentrically disposed with the first cylinder member 241 is disposed inside the first cylinder member 241. As illustrated in FIG. 3, a heat medium H, for example, water which has flowed in through the heat medium inflow port 202 passes through the flow paths (hollow portion) 32 of each of the hollow fiber membranes 31 of the hollow fiber membrane bundle 3B on the outer peripheral side of the first cylinder member 241, and the inside of the second cylinder member 245 in order, thereby being discharged through the heat medium outflow port 203. In addition, when the heat medium H passes through the flow paths 32 of each of the hollow fiber membranes 31, heat exchange (heating or cooling) is performed inside the blood flow path 33 between the hollow fiber membranes 31 and the blood B which comes into contact with the hollow fiber membranes 31.

The filter member 41A which has a function of capturing air bubbles present in the blood B flowing in the blood flow path 33 is disposed on the downstream side of the blood flow path 33.

The filter member 41A is configured with a substantially rectangular sheet-like member (hereinafter, will be simply referred to as "sheet" as well) and is formed by winding the sheet along the outer periphery of the hollow fiber membrane bundle 3A. Both end portions of the filter member 41A are also fixedly attached to the partition walls 8 and 9 respectively. Accordingly, the filter member 41A is fixed to the housing 2A (refer to FIG. 3). Note that, it is preferable that the filter member 41A is provided such that the inner peripheral surface comes into contact with the outer peripheral surface of the hollow fiber membrane bundle 3A and covers substantially the whole surface of the outer peripheral surface.

In addition, even if air bubbles are present in blood flowing in the blood flow path 33, the filter member 41A can capture the air bubbles (refer to FIG. 6). In addition, the air bubbles captured by the filter member 41A are driven by a blood flow and enter the inside of each of the hollow fiber membranes 31 in the vicinity of the filter member 41A. As a result thereof, the air bubbles are removed from the blood flow path 33.

In addition, a cylindrical gap is formed between the outer peripheral surface of the filter member 41A and the inner peripheral surface of the cylindrical housing main body 21A, and the gap forms a blood outflow side space 25A. The blood outflow side space 25A and the blood outflow port 28 communicating with the blood outflow side space 25A form a blood outflow portion. Since the blood outflow portion has the blood outflow side space 25A, a space for the blood B which has penetrated the filter member 41A and flows toward the blood outflow port 28 is ensured, and thus, the blood B can be smoothly discharged.

As illustrated in FIG. 3, a toric rib 291 is protrusively formed inside the first lid 22A. The first lid 22A, the rib 291, and the partition wall 8 define a first room 221a. The first room 221a is a gas outflow chamber from which the gas G flows out. The left end opening of each of the hollow fiber membranes 31 of the hollow fiber membrane bundle 3A is open to the first room 221a and communicates therewith. In the artificial lung 10, a gas outflow portion is configured with the gas outflow port 27 and the first room 221a. Meanwhile, a toric rib 292 is protrusively formed inside the second lid 23A as well. The second lid 23A, the rib 292, and the partition wall 9 define a second room 231a. The second room 231a is a gas inflow chamber to which the gas G flows in. The right end opening of each of the hollow fiber membranes 31 of the hollow fiber membrane bundle 3A is open to the second room 231a and communicates therewith. In the artificial lung 10, a gas inflow portion is configured with the gas inflow port 26 and the second room 231a.

A flow of blood in the artificial lung 10 of the present embodiment will now be described. In the artificial lung 10, the blood B which has flowed in through the blood inflow port 201 passes through the blood inflow side space 24A and the side hole 243 in order, thereby flowing into the heat exchange section 10B. In the heat exchange section 10B, while flowing in the blood flow path 33 in a downstream direction, the blood B comes into contact with an outer surface of each of the hollow fiber membranes 31 of the heat exchange section 10B such that heat exchange (heating or cooling) is performed. The blood B subjected to heat exchange as described above flows into the artificial lung section 10A.

In the artificial lung section 10A, the blood B flows further in the blood flow path 33 in the downstream direction. Meanwhile, gas (a gas mixture including oxygen) supplied through the gas inflow port 26 is distributed from the second room 231a to the flow paths 32 of each of the hollow fiber membranes 31 of the artificial lung section 10A and flows in the flow paths 32. Thereafter, the gas is integrated in the first room 221a and is discharged through the gas outflow port 27. The blood B flowing in the blood flow path 33 comes into contact with the outer surface of each of the hollow fiber membranes 31 of the artificial lung section 10A. Then, gas exchange, that is, oxygenation and decarbonation is performed between the flow paths 32 and the gas G flowing therein.

In a case where the blood B after gas exchange is intermixed with air bubbles, the air bubbles are captured by the filter member 41A, thereby being prevented from flowing out to the downstream side of the filter member 41A.

After the blood B is subjected to heat exchange and gas exchange in order and air bubbles are additionally removed, the blood B flows out through the blood outflow port 28.

Figure 7A:
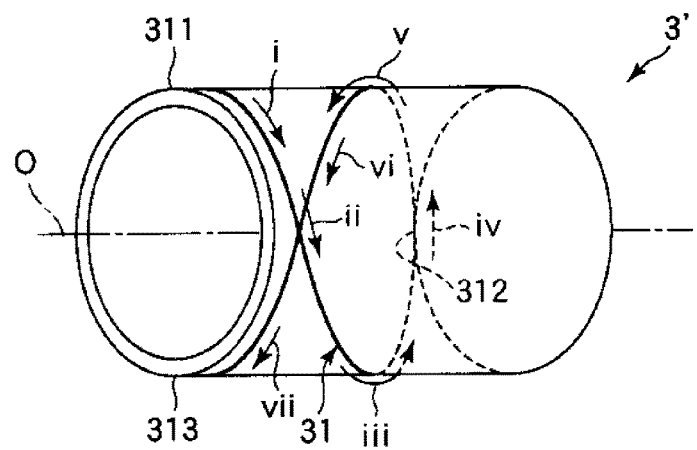
FIG. 7(a) is a perspective view illustrating a base material which serves as the hollow fiber membrane bundle.

A configuration of the hollow fiber membrane bundle 3A will now be described in detail. As mentioned above, the hollow fiber membrane bundle 3A is configured with multiple hollow fiber membranes 31. In addition, the hollow fiber membrane bundle 3A is obtained from a base material 3' which is obtained by winding the hollow fiber membranes 31 around a central axis O of the first cylinder member 241 (cylinder body) multiple times along the direction of the central axis O (refer to FIG. 7(a)).

Hereinafter, one hollow fiber membrane 31 will be representatively described. The hollow fiber membrane 31 starts being wound from a start point 311 on the left side in the direction of the central axis O and proceeds toward the right side. On the right side, the hollow fiber membrane 31 turns at a turning point 312. Thereafter, the hollow fiber membrane 31 returns to the left side again and arrives at an end point 313. In this manner, the hollow fiber membrane 31 is wound in the order of the arrows i→ii→iii→iv→v→vi→vii in FIG. 7(b).

During this one round trip, the hollow fiber membrane 31 is wound by a predetermined number N of rounds. In the illustrated configuration, N=1.5 is used. During one round trip, the hollow fiber membrane 31 makes 1.5 rounds around the central axis O. This is called "0.75 winds".

Note that, the hollow fiber membrane 31 is fixed by the action of fixing strings 11 (which will be described later) at both end portions of the first cylinder member 241. Accordingly, the winding is performed multiple times, and thus, the base material 3' can be obtained. In addition, the hollow fiber membrane bundle 3A can be obtained by cutting both end portions of the base material 3' including the fixing strings 11 as a whole.

As mentioned above, in the present invention, the hollow fiber membrane 31 having the inner diameter $\phi d_1$ and the outer diameter $\phi d_2$ which are relatively small is used. Particularly, since the outer diameter $\phi d_2$ of the hollow fiber membrane 31 is relatively small, a blood filling amount can be reduced. Meanwhile, when the inner diameter $\phi d_1$ is relatively small, a pressure loss of the gas G generally tends to increase.

Figure 7B:
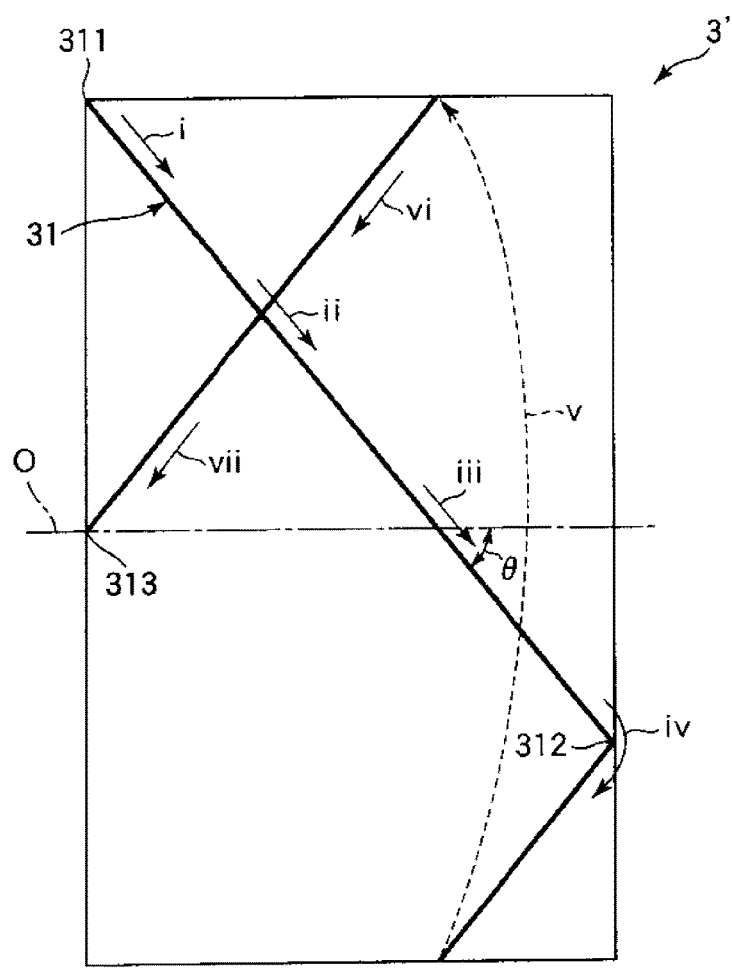
FIG. 7(b) is a development view illustrating the base material which serves as the hollow fiber membrane bundle.

Therefore, in the present invention, a tilt angle (lead angle) θ with respect to the central axis O is set to equal to or smaller than 60° (refer to FIG. 7(b)), and a ratio $\phi D_1/L$ of an outer diameter $\phi D_1$ of the hollow fiber membrane bundle 3A to a length L of the hollow fiber membrane bundle 3A is set to equal to or greater than 0.4 (refer to FIGS. 3 and 5). When these conditions are satisfied, the overall length of the hollow fiber membrane 31 can be relatively shortened. Thus, even if the hollow fiber membrane 31 having the relatively small inner diameter $\phi d_1$ is used, a pressure loss can be prevented or constrained. In other words, both reducing the blood filling amount and restraining an increase of the pressure loss of the gas G can be compatible.

The tilt angle θ preferably ranges from 30° to 60° and more preferably ranges from 40° to 50°. When the tilt angle θ is below the above-referenced lower limit value, the hollow fiber membrane 31 is required to be more firmly fixed by the fixing strings 11 at the end portions of the hollow fiber membrane bundle 3A, and it may be difficult to manufacture the base material 3'. Meanwhile, when the tilt angle θ exceeds the above-referenced upper limit value, the overall length of the hollow fiber membrane 31 is excessively elongated regardless of the size of the ratio φD$_1$/L, and there is concern that a pressure loss of the gas G may increase.

In addition, the ratio φD$_1$/L preferably ranges from 0.4 to 2.5 and more preferably ranges from 0.8 to 1.6. When the ratio φD$_1$/L is below the above-referenced lower limit value, even if the tilt angle θ is within the above-referenced range, the overall length of the hollow fiber membrane 31 becomes excessively elongated. Meanwhile, when the ratio φD$_1$/L exceeds the above-referenced upper limit value, the aforementioned number of windings becomes excessively small, and the hollow fiber membrane is unlikely to be wound.

In this manner, when being within the range of the above-referenced numerical values, the overall length of the hollow fiber membrane 31 can be appropriately ensured.

In addition, as illustrated in FIG. 5, the outer diameter (maximum outer diameter) φD$_1$ of the hollow fiber membrane bundle 3A preferably ranges from 20 mm to 200 mm and more preferably ranges from 40 mm to 150 mm. The inner diameter (the maximum inner diameter) φD$_2$ of the hollow fiber membrane bundle 3A preferably ranges from 10 mm to 150 mm and more preferably ranges from 20 mm to 100 mm. In addition, as illustrated in FIG. 3, the length L preferably ranges from 30 mm to 250 mm and more preferably ranges from 50 mm to 200 mm. When such conditions are met, the aforementioned effect can be reliably conducted.

Figure 11A:
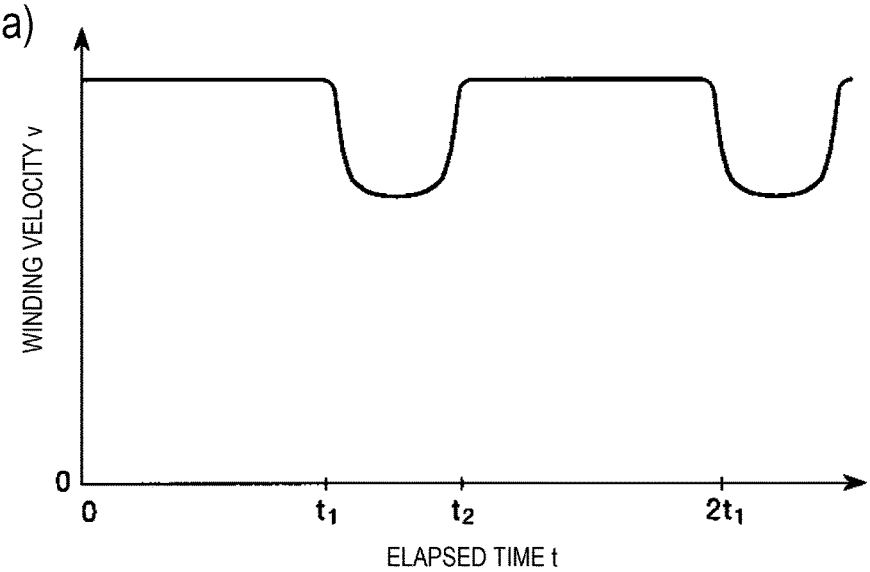
FIG. 11(a) is a graph illustrating a relationship between a winding velocity and an elapsed time in a case where a hollow fiber membrane is wound while a rotary velocity of a winding portion and a rotary velocity of a feeding portion are individually in a uniform state.

Here, in the present invention, since the tilt angle θ of the hollow fiber membrane 31 is relatively small, when turning at the end portion in a step of manufacturing the hollow fiber membrane bundle 3A, the winding velocity slightly falls (refer to FIG. 11(a)). When the winding velocity slightly falls, a tensile force of the hollow fiber membrane slightly changes. Depending on the degree of the change, for example, there is concern that the shape of the micropore may change (i.e., be distorted) in a case of the artificial lung section. As a result thereof, there is concern that the optimal gas exchange function that the hollow fiber membrane bundle 3A originally has may not be sufficiently exhibited.

Hereinafter, description will be given regarding a method of manufacturing the hollow fiber membrane bundle 3A in which the above-described disadvantages is prevented. First, the hollow fiber membrane bundle manufacturing apparatus used in the method of manufacturing the hollow fiber membrane bundle 3A will be described.

Figure 8:
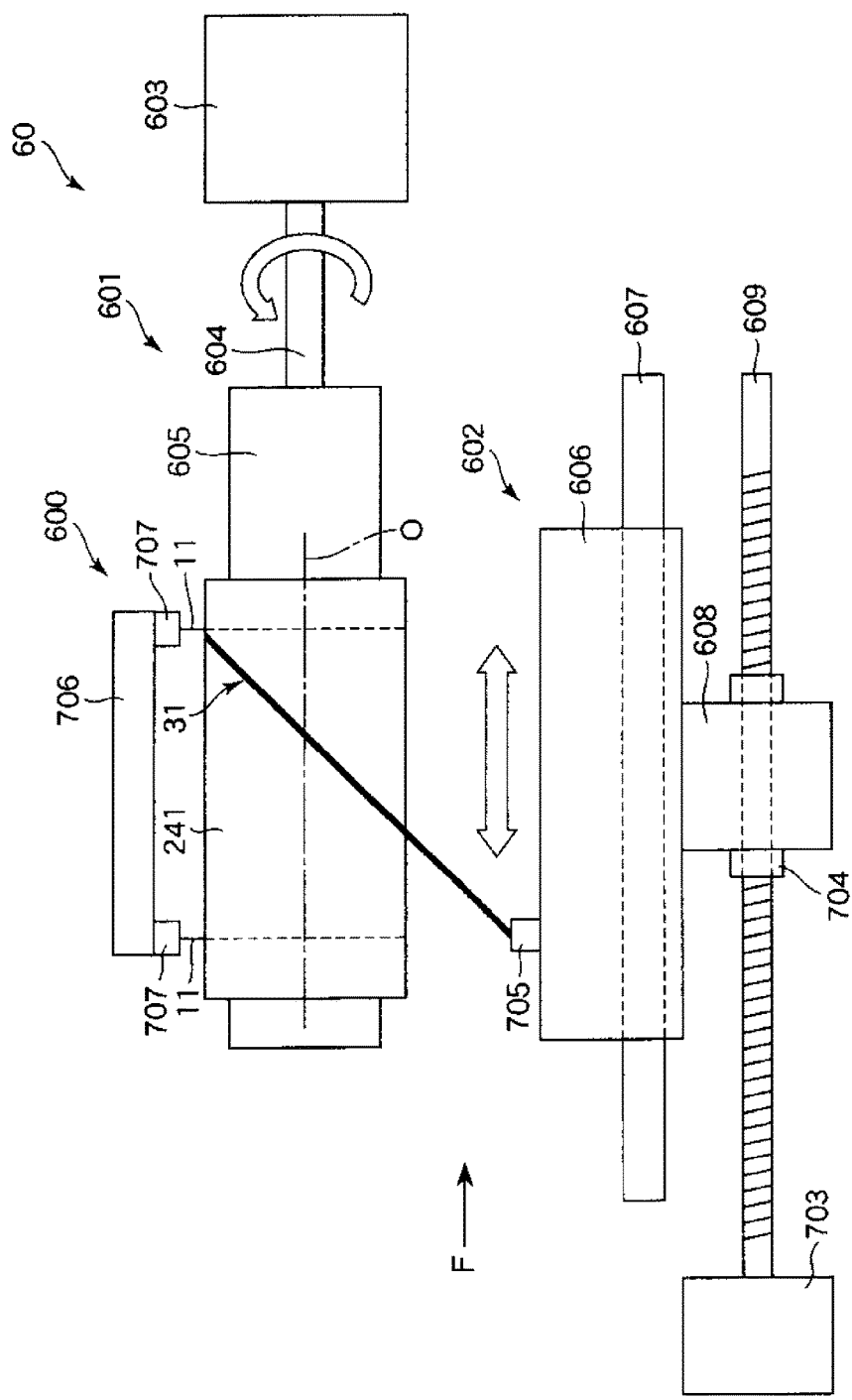
FIG. 8 is a view illustrating a hollow fiber membrane bundle manufacturing apparatus which is used when manufacturing the hollow fiber membrane bundle of the present invention.
Figure 9:
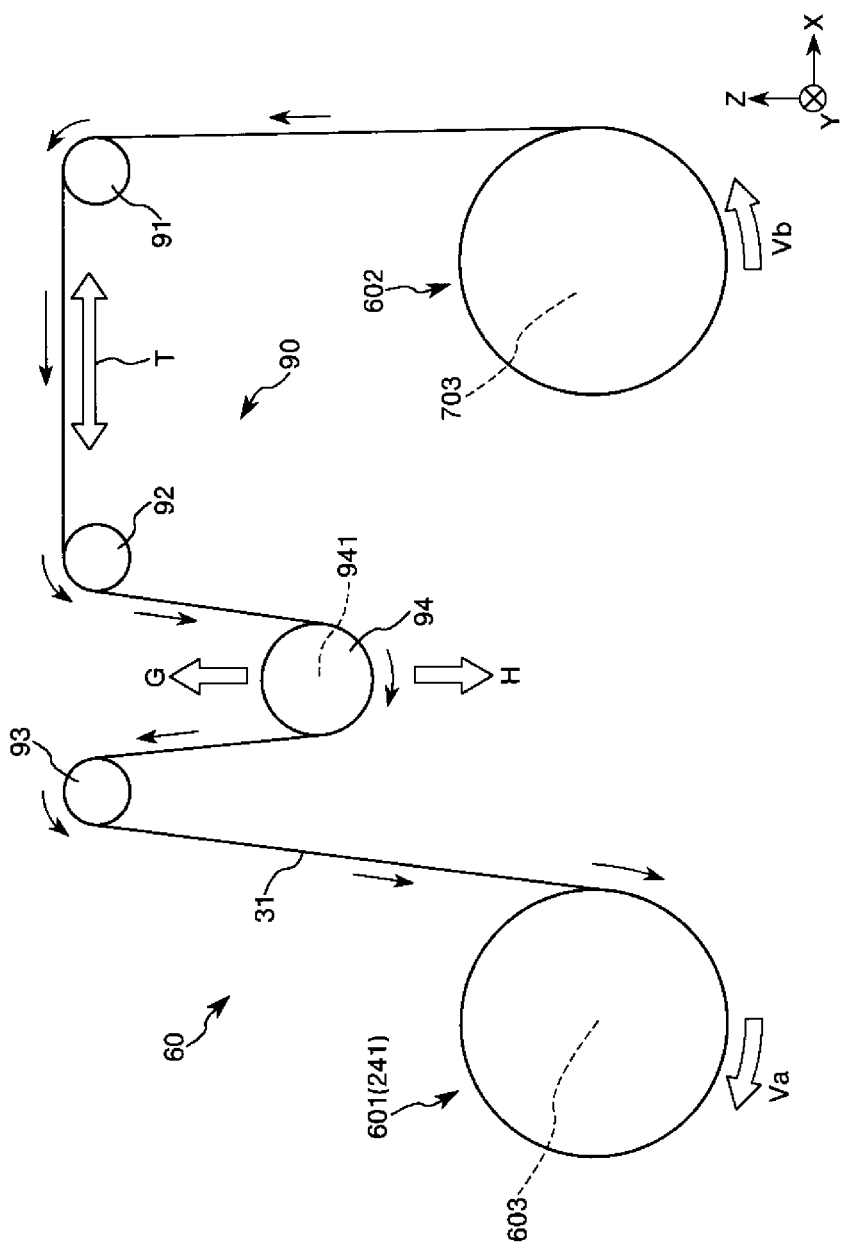
FIG. 9 is a schematic configuration diagram viewed in an arrow F direction in FIG. 8.
Figure 10:
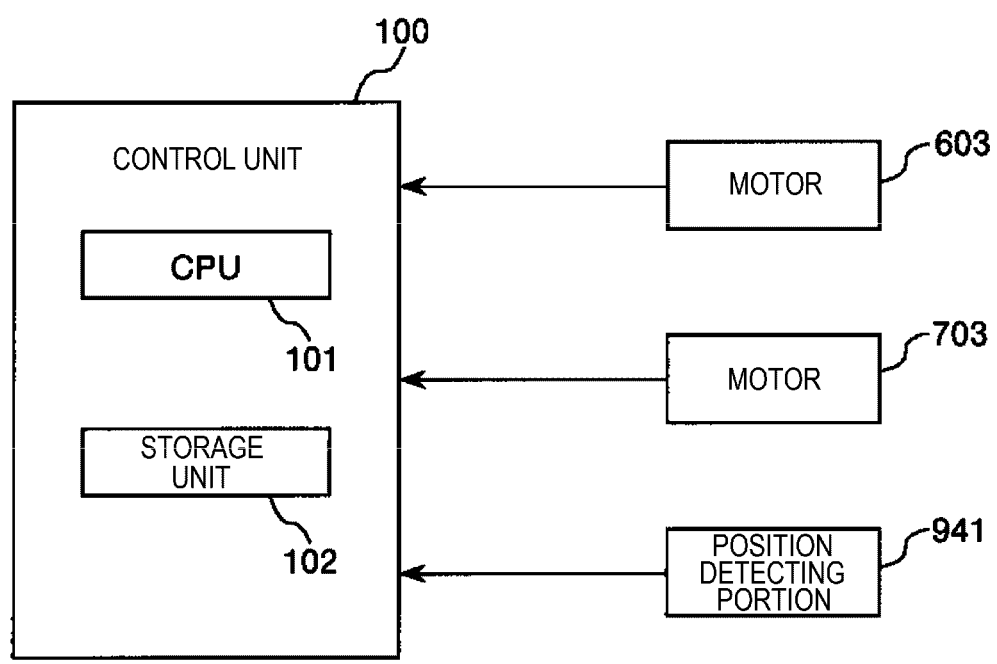
FIG. 10 is a block diagram illustrating the hollow fiber membrane bundle manufacturing apparatus illustrated in FIG. 8.

As illustrated in FIGS. 8 to 10, a winding apparatus 60 executes a method of manufacturing a hollow fiber membrane bundle according to the present invention and is provided with tubular core rotary means (winding portion) 601, a winding device (feeding portion) 602, a fixing device 600, a group of rollers 90, and a control unit (tensile force adjustment mechanism) 100 which controls driving thereof.

As illustrated in FIG. 8, the tubular core rotary means 601 is provided with a motor 603, a motor shaft 604, and a core attachment member 605 which is fixed to the motor shaft 604. The first cylinder member 241 which is a part of the housing 2A of the artificial lung 10 is attached to the core attachment member 605 and is rotated by the motor 603. The motor 603 is electrically connected to the control unit 100 and is controlled by the control unit 100 so as to be driven.

The winding device 602 is provided with a main body portion 606 including an accommodation portion which internally accommodates the hollow fiber membrane 31, and a discharge portion 705 discharging the hollow fiber membrane 31 and moving in an axial direction (transverse direction in FIG. 8) of the main body portion 606. Moreover, the main body portion 606 is fixed to a linear table 608 and a ball nut member 704 moving on a linear rail 607. When a motor 703 is driven and a ball screw shaft 609 rotates, the ball nut member 704 can move in parallel with the axial direction of the main body portion 606. The motor 703 can rotate normally and reversely, and is controlled by the control unit 100 so as to be driven.

The fixing device 600 is provided with a main body portion 706 including an accommodation portion which accommodates the fixing strings (string-like bodies) 11 for fixing the hollow fiber membrane 31 wound around the first cylinder member 241, and a discharge portion 707 discharging the fixing strings 11 toward both end portions of the first cylinder member 241. When the hollow fiber membrane 31 is fixed by using the fixing strings 11, the fixing strings 11 discharged from the discharge portion 707 are wound around the hollow fiber membrane 31 on the rotating first cylinder member 241, and the hollow fiber membrane 31 is fixed. After the hollow fiber membrane 31 is fixed, the fixing strings 11 adopted for the fixing are cut off from the fixing device 600 by a cutter (not illustrated).

The hollow fiber membrane 31 discharged and fed from the discharge portion 705 is wound around the first cylinder member 241 which rotates in accordance with an operation of the motor 603. When the discharge portion 705 feeds the hollow fiber membrane 31 while moving, for example, the hollow fiber membrane 31 starts being wound from one end portion of the first cylinder member 241, and when the hollow fiber membrane 31 is wound to the other end portion, the hollow fiber membrane 31 turns and can be wound toward the one end portion. A cylindrically shaped base material of the hollow fiber membrane bundle 3A can be obtained by repeating such winding multiple times. In the base material of the hollow fiber membrane bundle 3A, the portions of both end portions to which the hollow fiber membrane 31 is fixed by the fixing strings 11 are cut, and the base material is used as the hollow fiber membrane bundle 3A.

As illustrated in FIGS. 8 and 9, the group of rollers 90 has three fixed rollers 91, 92, and 93 which are provided between the tubular core rotary means 601 and the winding device 602, and a movable roller (detection portion) 94 which is movable in a Z-axis direction.

As illustrated in FIG. 9, the fixed roller 91 is provided on a positive Z-axis side of the winding device 602. The fixed roller 92 is provided on a negative X-axis side of the fixed roller 91. The fixed roller 93 is provided on the negative X-axis side of the fixed roller 92. In the winding apparatus 60, the hollow fiber membrane 31 is put around the fixed rollers 91, 92, and 93.

The movable roller 94 is positioned between the fixed rollers 92 and 93 and on a negative Z-axis side of the fixed rollers 92 and 93. Both ends of the movable roller 94 are free ends and are supported by the hollow fiber membrane 31 between the fixed rollers 92 and 93. Therefore, in the winding apparatus 60, the movable roller 94 is in a state of applying a tensile force T to the hollow fiber membrane 31 with the weight of itself.

Note that, the tensile force T is set to have a magnitude (hereinafter, will also be referred to as "suitable magnitude") to the extent that the hollow fiber membrane bundle 3A obtained by winding the hollow fiber membrane 31 can sufficiently exhibit its intended function. In addition, for example, the tensile force T can be adjusted by adjusting the weight of the movable roller 94 or biasing the movable roller 94 with a biasing member or the like to the positive Z-axis side or the negative Z-axis side.

In addition, the movable roller 94 is movable in the Z-axis direction in accordance with the relationship of the magnitude of the tensile force T. When the tensile force T becomes greater than that of the illustrated configuration, the movable roller 94 moves to the positive Z-axis side (arrow G direction in FIG. 9) as a result of the tensile force T in the hollow fiber membrane 31. Meanwhile, when the tensile force T becomes smaller than that of the illustrated configuration, the movable roller 94 moves to the negative Z-axis side (arrow H direction in FIG. 9) by the hollow fiber membrane 31.

In addition, as illustrated in FIG. 10, the movable roller 94 is provided with a position detection portion 941 which is electrically connected to the control unit 100 and detects a position (height). The control unit 100 can detect the position of the movable roller 94 based on a signal from the position detection portion 941 and calculate the magnitude of the tensile force T of the hollow fiber membrane 31 in accordance with the position.

In the winding apparatus 60, the tensile force T having the suitable magnitude is applied to the hollow fiber membrane 31 in advance, and the hollow fiber membrane 31 is wound in that state. Thus, it is possible to obtain the hollow fiber membrane bundle 3A which is wound with a suitable tensile force. In the present embodiment, an upper limit value $T_{max}$ and a lower limit value $T_{min}$ are set as a permissible range of the tensile force T having the suitable magnitude. When the condition of lower limit value $T_{min} \leq$ tensile force $T \leq$ upper limit value $T_{max}$ is satisfied, the tensile force T is considered to be the suitable magnitude.

As illustrated in FIG. 10, the control unit 100 is electrically connected to the motor 603 of the tubular core rotary means 601, the motor 703 of the winding device 602, and the position detection portion 941 of the movable roller 94. The control unit 100 has a function of controlling operations thereof. The control unit 100 has a central processing unit (CPU) 101 and a storage unit 102.

The CPU 101 executes a program for various types of processing. The storage unit 102 has an electrically erasable programmable read-only memory (EEPROM) which is a type of a non-volatile semiconductor memory, for example, and can store various types of programs and the like.

In addition, the storage unit 102 stores information such as the upper limit value $T_{max}$ and the lower limit value $T_{min}$ of the suitable magnitude of the tensile force T of the aforementioned hollow fiber membrane 31.

FIG. 11(a) is a graph illustrating a relationship between an elapsed time t from a start of winding, and a winding velocity v of the hollow fiber membrane 31. The term "winding velocity v" denotes a length of the hollow fiber membrane 31 actually wound per unit time. The graph is obtained while a rotary velocity $V_a$ of the motor 603 and a rotary velocity $V_b$ of the motor 703 are individually in a uniform state (corresponding to the winding operation near the longitudinal center of the base material, away from the ends where a reversal of direction occurs) and are experimentally measured in advance. Note that, the graph of FIG. 11(a) is a graph in a case of manufacturing the hollow fiber membrane having the inner diameter $\phi d_1$ of 150 μm through winding such that the tilt angle (lead angle) θ with respect to the central axis O becomes 45° and the ratio $\phi D_1/L$ becomes 1.0.

As illustrated in FIG. 11(a), it is found that the winding velocity v has changed (fallen) due to a reversal in the tilt angle (i.e., a reversal in the winding direction) during elapsed time $t_1$ to $t_2$. When a predetermined time further elapses from the elapsed time $t_2$, the winding velocity v exhibits a similar movement during a subsequent reversal. The movements are exhibited during the winding of the hollow fiber membrane 31 when the hollow fiber membrane 31 is positioned at the end portion of the first cylinder member 241, that is, when the hollow fiber membrane 31 is wound around the end portion.

Therefore, the storage unit 102 stores a calibration curve for cancelling a change of the winding velocity v, based on the relationship between the winding velocity v and the elapsed time t illustrated in FIG. 11(a). For example, the calibration curve is stored as an arithmetic expression or a table.

Figure 11B:
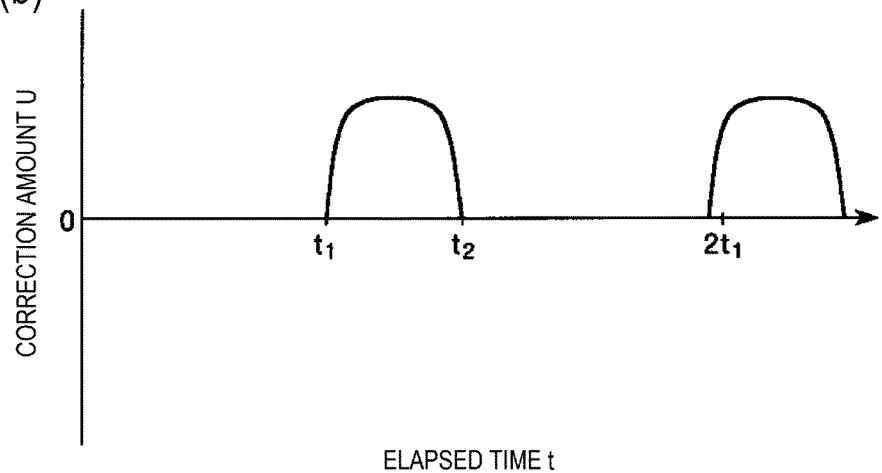
FIG. 11 (b) is a graph illustrating a relationship between a correction amount of the rotary velocity of the feeding portion and the elapsed time.

FIG. 11(b) is a graph showing the calibration curve while the vertical axis indicates a correction amount U of the rotary velocity $V_b$ of the motor 703 and the transverse axis indicates the elapsed time t. As illustrated in FIG. 11(b), during the elapsed time $t_1$ to $t_2$, the correction amount U of the rotary velocity $V_b$ has changed to an arch which is an overturned form of the line shape of the graph illustrated in FIG. 11(a), in accordance with the fall of the winding velocity v.

Figure 12:
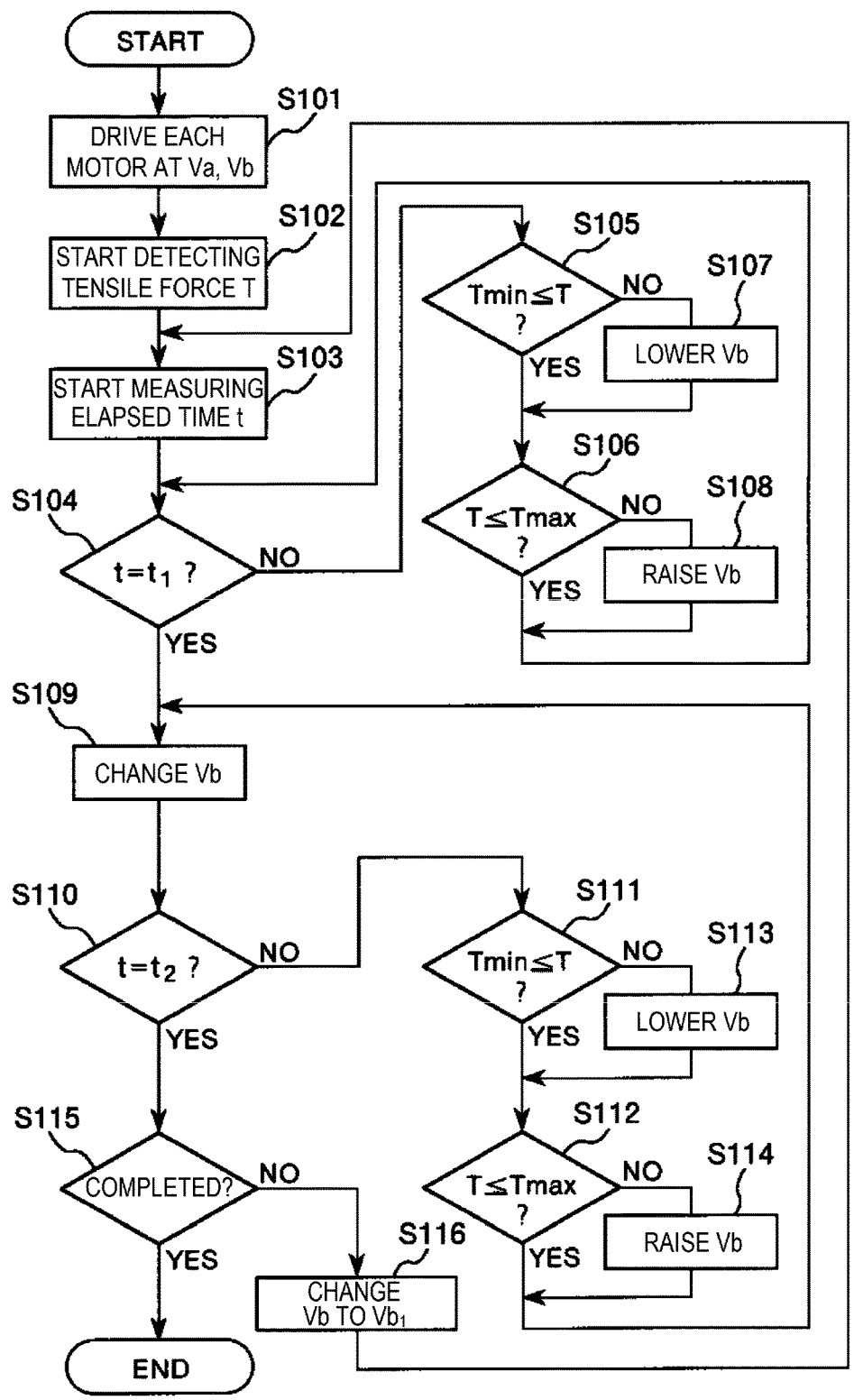
FIG. 12 is a flowchart for describing a control program of the hollow fiber membrane bundle manufacturing apparatus.

Subsequently, the control program of the control unit 100 will be described based on the flowchart of FIG. 12.

First, the hollow fiber membrane 31 is put around the fixed rollers 91, 92, and 93 and the movable roller 94 from the winding device 602, and in a state where the tip is fixed to the first cylinder member 241, the motor 603 and the motor 703 are rotated (Step S101). Accordingly, winding of the hollow fiber membrane 31 starts.

In this case, the rotary velocity $V_a$ of the motor 603 is a velocity $V_{a1}$, and the rotary velocity $V_b$ of the motor 703 is a velocity $V_{b1}$. Note that, in the present embodiment, the rotary velocity $V_a$ of the motor 603 is set to be uniform regardless of the elapsed time t.

In addition, winding is performed such that the tilt angle (lead angle) θ with respect to the central axis O of the hollow fiber membrane 31 becomes 45° and the ratio $\phi D_1/L$ becomes 1.0.

In addition, simultaneously with the driving of the motors 603 and 703, based on a signal from the position detection portion 941 of the movable roller 94, detection of the tensile force T of the hollow fiber membrane 31 between the tubular core rotary means 601 and the winding device 602 starts (Step S102).

Moreover, simultaneously with the driving of the motors 603 and 703, a timer is operated so as to measure the elapsed time t from the time the winding starts (Step S103).

In Step S104, it is determined whether or not the elapsed time $t=t_1$ is reached. In Step S104, in a case where it is determined that elapsed time $t=t_1$ is not yet reached, it is determined whether or not tensile force $T \geq T_{min}$ is established (Step S105). In Step S105, in a case where it is determined that tensile force $T \geq T_{min}$ is established, it is subsequently determined whether or not tensile force $T \leq T_{max}$ is established (Step S106). In Step S106, in a case where it is determined that tensile force $T \leq T_{max}$ is established, the tensile force T is the suitable magnitude. Therefore, the procedure returns to Step S104 again.

Here, in Step S105, in a case where it is determined that tensile force T<lower limit value $T_{min}$ is established, the rotary velocity $V_b$ of the motor 703 is reduced below $V_{b1}$, thereby establishing tensile force $T \geq T_{min}$ (Step S107). In addition, in Step S106, in a case where it is determined that tensile force $T > T_{max}$ is established, the rotary velocity $V_b$ of the motor 703 is raised above $V_{b1}$, thereby establishing tensile force $T \leq T_{max}$ (Step S108). Steps S105 to S108 are repeated until elapsed time $t=t_1$ is reached.

In Step S104, in a case where it is determined that elapsed time $t=t_1$ is reached, the rotary velocity $V_b$ of the motor 703 is changed (Step S109). In this case, the rotary velocity $V_b$ is changed based on the calibration curve illustrated in FIG. 11(b). Accordingly, it is possible to effectively prevent or restrain a change of the tensile force T caused by a fall of the winding velocity v. Thus, winding can be performed while the tensile force T of the hollow fiber membrane 31 is maintained so as to obtain the suitable magnitude as much as possible.

In Step S110, it is determined whether or not elapsed time $t=t_2$ is reached. In Step S110, in a case where it is determined that elapsed time $t=t_2$ is not yet reached, Steps S111 to S114 are repeatedly performed. Since Steps S111 to S114 are similar to Steps S105 to S108 mentioned above, description thereof will be omitted.

In Step S110, in a case where it is determined that elapsed time $t=t_2$ is reached, it is determined whether or not winding of the hollow fiber membrane 31 is completed (Step S115). Note that, for example, this determination is performed based on the total number of rotations of the motors 603 and 703, the elapsed time t, the remaining quantity of the hollow fiber membrane 31, and the like.

In a case where it is determined in Step S115 that winding of the hollow fiber membrane 31 is not completed, the rotary velocity $V_b$ of the motor 703 is changed to $V_{b1}$ (Step S116), winding is performed, and the procedure returns to Step S103.

The above-described control is repeated until it is determined in Step S115 that winding of the hollow fiber membrane 31 is completed.

In this manner, in the present embodiment, the rotary velocity $V_b$ of the motor 703 is adjusted based on the calibration curve of the elapsed time t and the winding velocity v. Accordingly, winding can be performed while the tensile force T of the hollow fiber membrane 31 is maintained so as to have the suitable magnitude.

Moreover, in the present embodiment, while the tensile force T is detected, an adjustment is made when the tensile force T deviates from the range between the lower limit value $T_{min}$ and the upper limit value $T_{max}$. Accordingly, winding can be performed while the tensile force T of the hollow fiber membrane 31 is more reliably maintained so as to have the effectively suitable magnitude.

Hereinbefore, in this manufacturing method, the hollow fiber membrane bundle 3A obtained through winding which is performed while the tensile force T of the hollow fiber membrane 31 is adjusted can reliably exhibit the excellent original gas exchange function.

Note that, in the present embodiment, as the suitable magnitude of the tensile force T of the hollow fiber membrane 31, the lower limit value $T_{min}$ and the upper limit value $T_{max}$ are set. However, it is preferable that the value of the lower limit value $T_{min}$ is set to be slightly greater than the lower limit value of the suitable magnitude of the actual tensile force T, and it is preferable that the value of the upper limit value $T_{max}$ is set to be slightly smaller than the upper limit value of the actual tensile force T. Accordingly, winding of the hollow fiber membrane 31 can be performed while the tensile force T is more reliably maintained so as to have the suitable magnitude.

Second Embodiment

Figure 13:
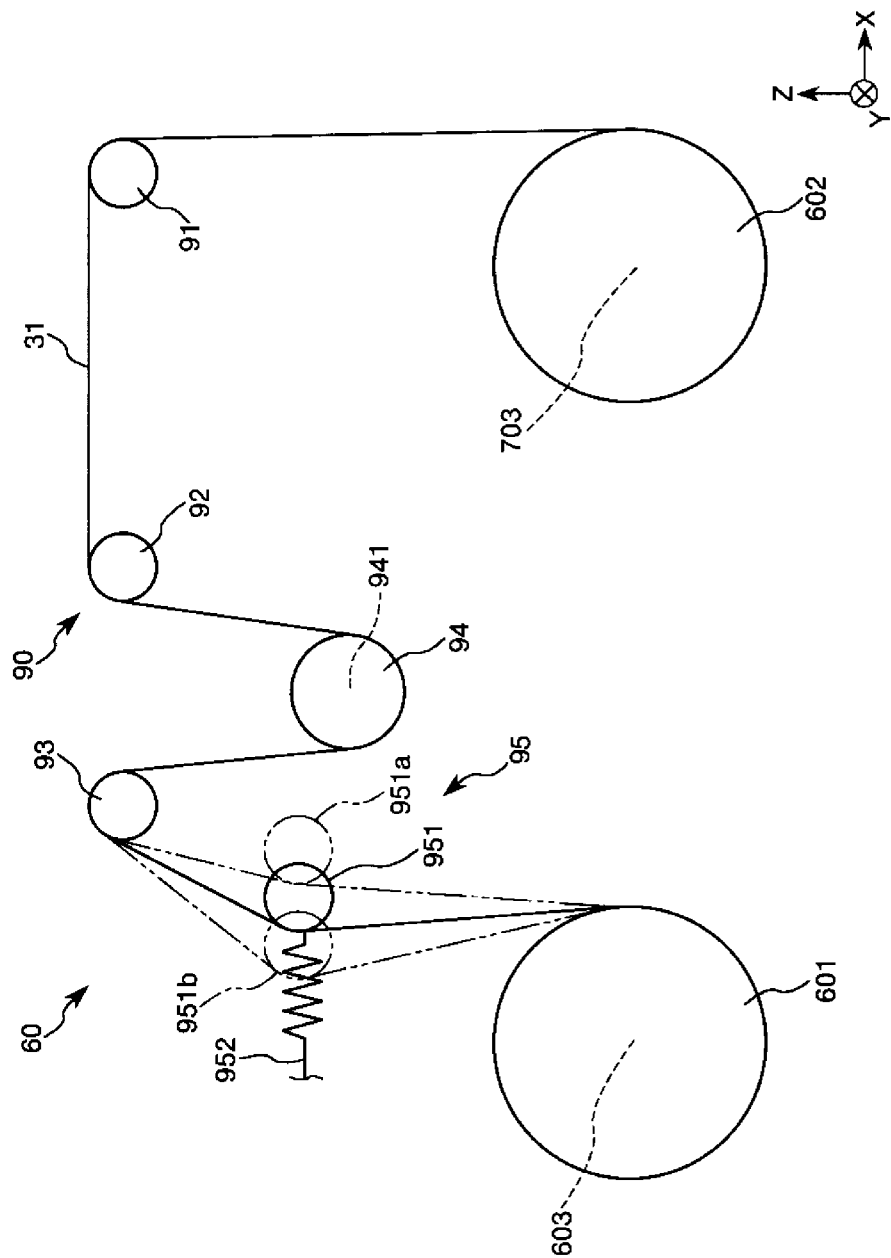
FIG. 13 is a schematic configuration diagram illustrating a hollow fiber membrane bundle manufacturing apparatus (second embodiment) which is used when manufacturing the hollow fiber membrane bundle of the present invention.

FIG. 13 is a schematic configuration diagram illustrating a hollow fiber membrane bundle manufacturing apparatus (second embodiment) which is used when manufacturing the hollow fiber membrane bundle of the present invention.

Hereinafter, with reference to FIG. 13, the second embodiment of a hollow fiber membrane bundle and a method of manufacturing a hollow fiber membrane bundle according to the present invention will be described. However, description will be given while focusing on points different from those of the aforementioned embodiment, and description of similar items will be omitted. The present embodiment is similar to the first embodiment except that an engagement portion is provided.

As illustrated in FIG. 13, a tensile force adjustment roller (engagement portion) 95 as the tensile force adjustment mechanism is provided between the tubular core rotary means 601 and the fixed roller 93. In addition, the tensile force adjustment roller 95 is provided with a roller main body 951 which is attached to the hollow fiber membrane 31, a biasing portion 952 which biases the roller main body 951 in an X-axis direction.

In addition, for example, the biasing portion 952 is configured with a coil spring, and the hollow fiber membrane 31 is put around the biasing portion 952 in a tensile state tensed further than the natural state. Therefore, the hollow fiber membrane 31 is tensed by the roller main body 951 in the negative X-axis side.

In a case where the tensile force T increases, the hollow fiber membrane 31 moves the roller main body 951 to a positive X-axis side (in FIG. 13, position indicated by a roller main body 951a) against a biasing force of the biasing portion 952. In this case, the hollow fiber membrane 31 between the fixed roller 93 and the tubular core rotary means 601 becomes close to a shape of a straight line compared to the state illustrated with the solid line in FIG. 13, and thus, the tensile force T can be restrained or prevented from increasing.

Meanwhile, in a case where the tensile force T is lessened, the hollow fiber membrane 31 is tensed and moved together with the roller main body 951 to the negative X-axis side (in FIG. 13, position indicated by a roller main body 951b) by the biasing portion 952. Accordingly, the hollow fiber membrane 31 between the fixed roller 93 and the tubular core rotary means 601 is further tensed by the biasing portion 952 compared to the state indicated by the solid line in FIG. 13. Thus, the tensile force T can be restrained or prevented from being lessened.

According to such a tensile force adjustment roller 95, compared to the first embodiment, the tensile force of the hollow fiber membrane 31 can be more reliably prevented or restrained from changing.

Third Embodiment

Figure 14:
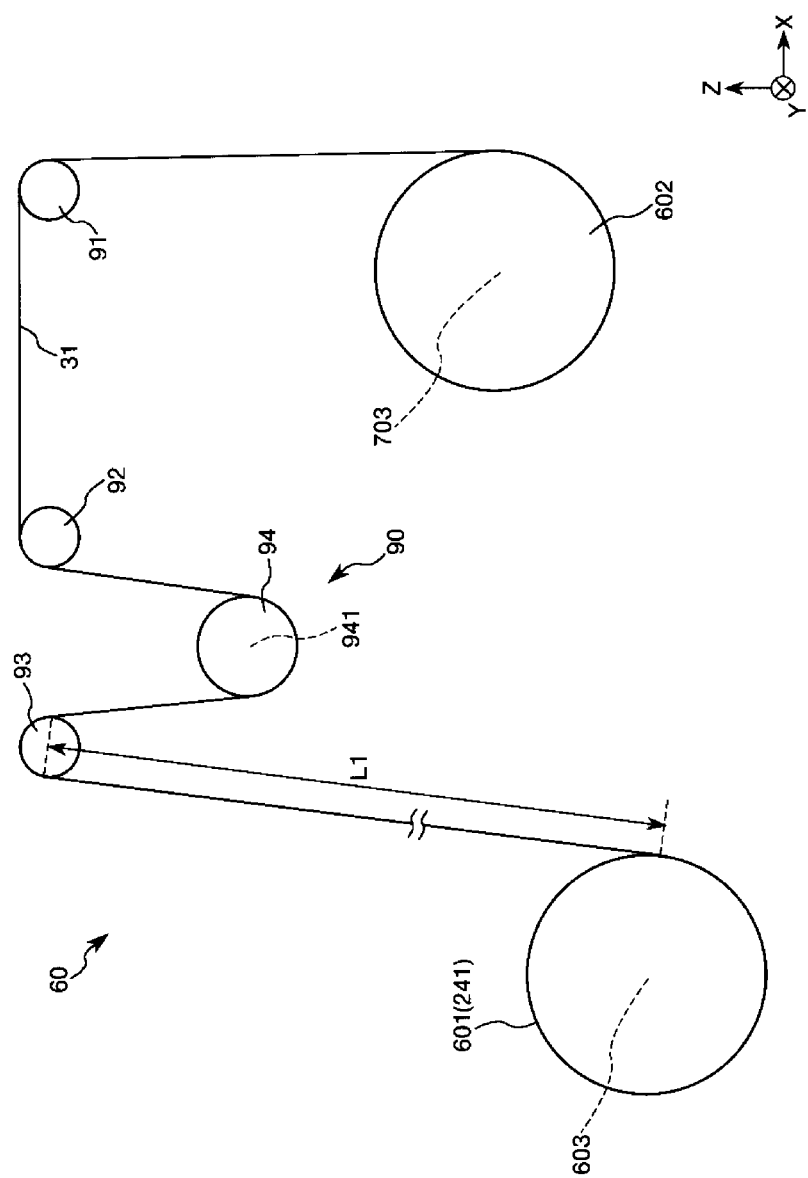
FIG. 14 is a schematic configuration diagram illustrating a hollow fiber membrane bundle manufacturing apparatus (third embodiment) which is used when manufacturing the hollow fiber membrane bundle of the present invention.

FIG. 14 is a schematic configuration diagram illustrating a hollow fiber membrane bundle manufacturing apparatus (third embodiment) which is used when manufacturing the hollow fiber membrane bundle of the present invention.

Hereinafter, with reference to FIG. 14, the third embodiment of a hollow fiber membrane bundle and a method of manufacturing a hollow fiber membrane bundle according to the present invention will be described. However, description will be given while focusing on points different from those of the aforementioned embodiments, and description of similar items will be omitted.

The present embodiment is similar to the first embodiment except that the tubular core rotary means is differently positioned.

As illustrated in FIG. 14, the tubular core rotary means 601 is positioned on the negative Z-axis side compared to the position in each of the embodiments described above. Therefore, a length L1 of the hollow fiber membrane 31 between the fixed roller 93 and the tubular core rotary means 601 is longer than the length of the hollow fiber membrane 31 between the fixed roller 93 and the tubular core rotary means 601 in the first embodiment.

The length L1 preferably ranges from 500 mm to 5,000 mm and more preferably ranges from 1,000 mm to 3,000 mm. In addition, the length L1 preferably ranges from 10 to 200 times the outer diameter of the first cylinder member 241 and more preferably ranges from 15 to 150 times thereof.

According to the present embodiment, even if the tensile force T changes, and the length of the hollow fiber membrane 31 slightly changes, it is possible to ensure a length to the extent that the amount of change can be sufficiently ignored. Thus, it is possible to obtain an effect similar to that of each of the embodiments described above.

Hereinbefore, the illustrated embodiments of the hollow fiber membrane bundle and the method of manufacturing a hollow fiber membrane bundle according to the present invention have been described. However, the present invention is not limited thereto. An arbitrary step may be added to the method of manufacturing a hollow fiber membrane bundle. In addition, each of the sections configuring the hollow fiber membrane bundle can be replaced with a section having an arbitrary configuration which can exhibit a similar function. In addition, an arbitrarily configured element may be added.

In addition, the hollow fiber membrane bundle and the method of manufacturing a hollow fiber membrane bundle according to the present invention may be realized by combining two or more arbitrary configurations (features) from each of the embodiments described above.

In addition, regarding the artificial lung section and the heat exchange section, the heat exchange section is disposed inside and the artificial lung section is disposed outside in the embodiments described above. However, without being limited thereto, the artificial lung section may be disposed inside and the heat exchange section may be disposed outside. In this case, blood flows down from the outside toward the inside.

In addition, in each of the embodiments described above, the tensile force of the winding hollow fiber membrane is adjusted by causing the rotary velocity of the winding portion to be uniform and adjusting the rotary velocity of the feeding portion. However, in the present invention, without being limited thereto, the tensile force thereof may be adjusted by causing the rotary velocity of the feeding portion to be uniform and adjusting the rotary velocity of the winding portion. In addition, the rotary velocities of both the winding portion and the feeding portion may be adjusted.

In addition, in the second embodiment, the engagement portion (attachment portion) is configured to be movable by the biasing portion. However, in the present invention, without being limited thereto, the biasing portion may be omitted and the engagement portion may be configured to be movable through control actions performed by the control unit.

In addition, in each of the embodiments described above, determining whether or not winding of the hollow fiber membrane is completed may be frequently performed or may be performed every predetermined time. In addition, in a case where it is determined that winding of the hollow fiber membrane is completed, the winding may be immediately stopped or the winding may be stopped after the winding is performed to the end portion of the first cylinder member.

In addition, in each of the embodiments described above, a biasing portion may be provided in the detection portion. In this case, the detection portion can exhibit a function similar to that of the engagement portion.

In addition, as described above, in a case where multiple engagement portions are provided in the tensile force adjustment mechanism, it is preferable that the engagement portions are configured to move in directions different from each other. Accordingly, the tensile force of the hollow fiber membrane can be more effectively prevented from changing.

In addition, in the second embodiment, the biasing portion is configured with the coil spring. However, in the present invention, without being limited thereto, for example, the biasing portion may be a leaf spring or a disk spring having a biasing force.

In addition, in the second embodiment, the biasing portion functions as a tension spring in which the hollow fiber membrane is put around in a tensile state tensed further than the natural state. However, the present invention is not limited thereto. For example, the hollow fiber membrane may be put around in a compression state compressed further than the natural state. In this case, the coil spring functions as a pressing spring.

In addition, in each of the embodiments described above, only one hollow fiber membrane is illustrated. However, in the present invention, multiple hollow fiber membranes may be wound around the same cylinder member at the same time.

Hereinafter, specific examples of the present invention will be described. Note that, the present invention is not limited thereto.

Example 1

An artificial lung section for artificial heart and lung illustrated in FIGS. 1 to 5 was prepared. In the artificial lung section for artificial heart and lung, the housing was formed of polycarbonate. The inside dimension of the housing was $\phi 90 \times 80$ mm.

The hollow fiber membrane was formed of polypropylene. In addition, the inner diameter $\phi d_1$ of the hollow fiber membrane, the tilt angle $\theta$, the ratio $\phi d_1/L$, the outer diameter $\phi D_1$ of the hollow fiber membrane bundle, the length L of the hollow fiber membrane bundle, the outer diameter $\phi d_2$ of the hollow fiber membrane, and the inner diameter $\phi D_2$ of the hollow fiber membrane bundle were set as shown in Table 1.

Example 2

An artificial lung section for artificial heart and lung of Example 2 was obtained under conditions similar to those of Example 1 except that the inner diameter $\phi d_1$ of the hollow fiber membrane, the tilt angle $\theta$, the ratio $\phi d_1/L$, the outer diameter φd₁ of the hollow fiber membrane bundle, the length L of the hollow fiber membrane bundle, the outer diameter φd₂ of the hollow fiber membrane, and the inner diameter φD₂ of the hollow fiber membrane bundle were set as shown in Table 1.

Example 3

An artificial lung section for artificial heart and lung of Example 3 was obtained under conditions similar to those of Example 1 except that the inner diameter φd₁ of the hollow fiber membrane, the tilt angle θ, the ratio φd₁/L, the outer diameter φD₁ of the hollow fiber membrane bundle, the length L of the hollow fiber membrane bundle, the outer diameter φd₂ of the hollow fiber membrane, and the inner diameter φD₂ of the hollow fiber membrane bundle were set as shown in Table 1.

Example 4

An artificial lung section for artificial heart and lung of Example 4 was obtained under conditions similar to those of Example 1 except that the inner diameter φd₁ of the hollow fiber membrane, the tilt angle θ, the ratio φd₁/L, the outer diameter φD₁ of the hollow fiber membrane bundle, the length L of the hollow fiber membrane bundle, the outer diameter φd₂ of the hollow fiber membrane, and the inner diameter φD₂ of the hollow fiber membrane bundle were set as shown in Table 1.

Comparative Example 1

An artificial lung section for artificial heart and lung of Comparative Example 1 was obtained under conditions similar to those of Example 1 except that the inner diameter φd₁ of the hollow fiber membrane, the tilt angle θ, the ratio φd₁/L, the outer diameter φD₁ of the hollow fiber membrane bundle, the length L of the hollow fiber membrane bundle, the outer diameter φd₂ of the hollow fiber membrane, and the inner diameter φD₂ of the hollow fiber membrane bundle were set as shown in Table 1.

Comparative Example 2

An artificial lung section for artificial heart and lung of Comparative Example 2 was obtained under conditions similar to those of Example 1 except that the inner diameter φd₁ of the hollow fiber membrane, the tilt angle θ, the ratio φd₁/L, the outer diameter φD₁ of the hollow fiber membrane bundle, the length L of the hollow fiber membrane bundle, the outer diameter φd₂ of the hollow fiber membrane, and the inner diameter φD₂ of the hollow fiber membrane bundle were set as shown in Table 1.

(Evaluation)

In a simulative usage state, with respect to the artificial lung sections for artificial heart and lung of Examples 1 to 4 and Comparative Examples 1 and 2, the transferability of oxygen, the filling amount of blood (maximum) filling the artificial lung section for artificial heart and lung, and the pressure loss (maximum) of the gas G in the hollow fiber membrane bundle were measured based on the regulations of ISO7199 (2009).

The aforementioned transferability of oxygen indicates the movement amount (mL/min) of oxygen when the quantity of flowing blood per minute is 7 L, and the pressure loss of the gas G indicates the pressure loss (mmH₂O) when the quantity of flowing gas per minute is 7 L. In addition, regarding each of the quantity of flowing blood per minute and the quantity of flowing gas per minute, the maximum flow rate when the artificial lung is in actual use is postulated.

Moreover, with respect to the artificial lung sections for artificial heart and lung of Examples 1 to 4 and Comparative Examples 1 and 2, whether or not each of the artificial lung sections for artificial heart and lung is suitable for actual use is generally evaluated in accordance with the following evaluation criterion 1 wherein:

A: remarkably excellent compared to the existing artificial lung sections for artificial heart and lung, B: excellent compared to the existing artificial lung sections for artificial heart and lung, and C: equal to or poor compared to the existing artificial lung sections for artificial heart and lung.

TABLE 1

|  | Comparative Example 1 | Example 1 | Example 2 | Example 3 | Example 4 | Comparative Example 2 |
|---|---|---|---|---|---|---|
| Inner diameter φd₁ [μm] of hollow fiber membrane | 50 | 90 | 100 | 130 | 150 | 170 |
| Tilt angle (lead angle) θ [°] | 70 | 60 | 50 | 40 | 30 | 20 |
| Ratio φD₁/L | 0.2 | 0.4 | 0.8 | 1.6 | 2.5 | 3 |
| Outer diameter φD₁ [mm] of hollow fiber membrane bundle | 10 | 20 | 40 | 150 | 200 | 250 |
| Length L | 50 | 50 | 50 | 94 | 80 | 83 |
| Outer diameter φd₂ [μm] of hollow fiber membrane | 100 | 120 | 150 | 200 | 220 | 250 |
| Inner diameter φD₂ of hollow fiber membrane bundle | 200 | 150 | 100 | 20 | 10 | 5 |
| Transferability of oxygen [mL/min] | 460 | 460 | 460 | 460 | 460.00 | 460 |
| Blood filling amount [mL] | 36 | 40.0 | 47 | 60 | 71 | 85 |
| Pressure loss [mmH₂O] of gas | 4000 | 200.0 | 95 | 128 | 38 | 22 |
| Evaluation | C | B | A | A | B | C |

As is clear from Table 1, according to the result, the artificial lung sections for artificial heart and lung of Examples 2 and 3 among Examples 1 to 4 are remarkably suitable for actual use, followed by the artificial lung sections for artificial heart and lung of Examples 1 and 4 to be suitable for actual use.

Note that, according to the present invention, as long as the inner diameter of the hollow fiber membrane is set to equal to or smaller than 150 μm, the tilt angle θ is set to equal to or smaller than 60°, and the ratio φD₁/L of the outer diameter D of the hollow fiber membrane bundle to the length L of the hollow fiber membrane bundle 3A is set to equal to or greater than 0.4, it has been determined that a hollow fiber membrane for artificial heart and lung which is more excellent than the existing hollow fiber membranes for artificial heart and lung can be obtained.

In addition, in the description above, the present invention has been described with reference to favorable embodiments. However, the present invention is not limited to the embodiments described above, and there is no need to mention that various modifications and changes can be made without departing from the gist and the scope of the present invention.

A hollow fiber membrane bundle of the present invention is a hollow fiber membrane bundle that is used in an artificial lung, includes integrated hollow fiber membranes having hollow portions through which a fluid passes, and exhibits a shape of a cylinder body as a whole shape. The hollow fiber membrane is tilted with respect to a central axis of the cylinder body and is wound around the central axis of the cylinder body. An inner diameter $\phi d_1$ of the hollow fiber membrane is equal to or smaller than 150 μm. A tilt angle θ with respect to the central axis of the cylinder body of the hollow fiber membrane is equal to or smaller than 60°. A ratio $\phi D_1/L$ of an outer diameter $\phi D_1$ of the cylinder body to a length L of the cylinder body is equal to or greater than 0.4. Therefore, while an increase of a pressure loss of the fluid inside the hollow fiber membrane is reduced, a blood filling amount can also be reduced, and thus, a burden to a patient can be reduced.

What is claimed is:

1. A method of manufacturing a hollow fiber membrane bundle configured to be used in an artificial lung and comprised of integrated hollow fiber membranes having hollow portions through which a fluid passes, the hollow fiber membrane bundle exhibiting a shape of a cylinder body as a whole shape, the method comprising the steps of:

winding the hollow fiber membrane around a central axis of the cylinder body along a longitudinal center portion of the cylinder body using a predetermined winding velocity corresponding to a length of the hollow fiber membrane being wound per unit time, wherein the winding includes feeding the hollow fiber membrane from a discharge portion of a winding device moving axially at a predetermined feeding velocity between first and second ends of the cylinder body such that the hollow fiber membrane is wound by at least 0.75 winds between the first and second ends, wherein the hollow fiber membrane has an inner diameter $\phi d_1$ equal to or smaller than 150 μm, wherein the hollow fiber membrane is wound around a central axis of the cylinder body such that a tilt angle θ with respect to the central axis of the cylinder body becomes equal to or smaller than 60°, and wherein a ratio $\phi D_1/L$ of an outer diameter $\phi D_1$ of the cylinder body to a length L of the cylinder body becomes equal to or greater than 0.4; and winding the hollow fiber membrane around the central axis of the cylinder body at the first and second ends of the cylinder body during a reversal of the tilt angle using an increased feeding velocity.

2. The method of claim 1 further comprising the steps of:
detecting a tensile force of the hollow fiber membrane being wound to the cylinder body; and
adjusting the feeding velocity during winding of the longitudinal center portion of the cylinder body to maintain the tensile force between an upper limit value and a lower limit value.

* * * * *